(12) United States Patent
Läufer et al.

(10) Patent No.: US 9,078,844 B2
(45) Date of Patent: Jul. 14, 2015

(54) COMBINATION OF A BACTERIAL CELL AND A BIOLOGICALLY ACTIVE AGENT

(75) Inventors: Albrecht Läufer, Hannover (DE); Bernd Eisele, Laatzen (DE); Leander Grode, Braunschweig (DE)

(73) Assignee: VAKZINE PROJEKT MANAGEMENT GMBH, Hannover (DE)

( * ) Notice: Subject to any disclaimer, the term of this patent is extended or adjusted under 35 U.S.C. 154(b) by 1107 days.

(21) Appl. No.: 11/577,498

(22) PCT Filed: Oct. 16, 2005

(86) PCT No.: PCT/EP2005/011127
§ 371 (c)(1),
(2), (4) Date: Feb. 4, 2008

(87) PCT Pub. No.: WO2006/045468
PCT Pub. Date: May 4, 2006

(65) Prior Publication Data
US 2008/0292656 A1 Nov. 27, 2008

(30) Foreign Application Priority Data
Oct. 21, 2004 (EP) .................................... 04025096

(51) Int. Cl.
*A61K 39/00* (2006.01)
*A61K 39/04* (2006.01)
*A61K 39/005* (2006.01)
*A61K 39/39* (2006.01)

(52) U.S. Cl.
CPC ........... *A61K 39/005* (2013.01); *A61K 39/0011* (2013.01); *A61K 39/39* (2013.01); *A61K 2039/55544* (2013.01)

(58) Field of Classification Search
None
See application file for complete search history.

(56) References Cited

U.S. PATENT DOCUMENTS

| | | | |
|---|---|---|---|
| 6,673,353 B1 * | 1/2004 | Kaufmann et al. | 424/200.1 |
| 7,670,788 B2 * | 3/2010 | Atassi | 435/7.1 |
| 7,988,980 B2 * | 8/2011 | Grode et al. | 424/248.1 |
| 2005/0169900 A1 * | 8/2005 | Gansbacher | 424/93.21 |
| 2010/0112610 A1 * | 5/2010 | Atassi | 435/7.93 |

FOREIGN PATENT DOCUMENTS

| | | |
|---|---|---|
| EP | 0902086 A1 | 3/1999 |
| JP | 2001-514000 A | 9/2001 |
| JP | 2002-537830 A | 11/2002 |
| WO | 94/18995 A1 | 9/1994 |
| WO | WO 0054783 * | 9/2000 |
| WO | 2004/094469 A1 | 11/2004 |

OTHER PUBLICATIONS

Murray et al. Proc. Natl. Acad. Sci. USA 93: 934-939, 1996.*
Tu et al. Weed Control Methods Handbook, The Nature Conservancy, Chapter 8, pp. 8.1-8.25, 2003.*
Bloemena et al., "Delayed-Type Hypersensitivity Reactions to Tumor-associated Antigens in Colon Carcinoma Patients Immunized with an Autologous Tumor Cell/Bacillus Calmette-Guerin Vaccine," Cancer Res. 1993, 53:456-459, publ. online Feb. 1, 1993.
Grode et al.. "Cell-mediated immunity induced by recombinant *Mycobacterium bovis* Bacille Calmette-Guerin strains against an interacellular bacterial pathogen: Importance of antigen secretion or membrane-targed antigen display as lipoprotein for vaccine efficacy," J Immunology 2002, 168(4):1869-1876; ISSN: 0022-1767.
Grode et al., "Increased vaccine efficacy against tuberculosis of recombinant *Mycobacterium bovis* bacille Calmette-Guerin mutants that secrete listeriolysin" J Clinical Investigation 2005, 115(9):2472-2479; ISSN 0021-9738.
Hess et al., "*Mycobacterim bovis* bacille Calmette-Guerin strains secreting listeriolysin of *Lysteria monocytogenes*," National Academy of Science 1998, 95:5299-5304 XP 002090837; ISSN: 0027-8424, 5302.
Matsumoto et al., "Recombinant *Mycobacterim bovis* bacillus Calmette-Guerin secreting merozoite surface protein 1 (MSP1) induces protection against rodent malaria parasite infection depending on MSP1-stimulated Interferon gamma and parasite-specific antibodies," J Exp Med 1998, 188(5):845-854 XP001260642; ISSN: 0022-1007.
Reyrat et al., "Urease Activity Does Not Contribute Dramatically to Persistence of *Mycobacterium bovis* Bacillus Calmette-Guerin," Infection and Immunity Sep. 1996, 64(9):3934-3936.
Sendide et al., "*Mycobacterium bovis* BCG Urease Attenuate Major Histocompatibility Complex Calls II Trafficking to the Macrophage Cell Surface," Infection and Immunity Jul. 2004, 72(7):4200-4209.
International Search Report and Written Opinion, PCT/EP2005/011127, mailed Jan. 16, 2006.
International Preliminary Report on Patentability, completed Sep. 14, 2006.

\* cited by examiner

*Primary Examiner* — S. Devi
(74) *Attorney, Agent, or Firm* — Faegre Baker Daniels LLP

(57) ABSTRACT

The present invention is related to a combination comprising a first constituent and a second constituent, wherein the first constituent is a bacterial cell which comprises at least one recombinant nucleic acid molecule encoding a phagolysosomal escape peptide or polypeptide; and wherein the second constituent is a biologically active agent. In certain embodiments, the combination is of use as a vaccine to induce an immune response in a mammal.

18 Claims, 5 Drawing Sheets

Experiment 3: Immunisation scheme 1: Gr. HV3.2 - HV3.4 and HV3.11 – HV3.13

Experiment 3: Immunisation scheme 2: Gr. HV3.5 – HV3.7 as well as HV3.14 – HV3.16

Experiment 3: Immunisation scheme 3: Gr. HV3.8 – HV3.10 as well as HV3.17 – HV3.19

Experiment 4: Immunisation scheme 1: Gr. HV4.2 – HV4.4 and HV4.11 – HV4.13

Experiment 4: Immunisation scheme 2: Gr. HV4.5 – HV4.7 as well as HV4.14 – HV4.16

Experiment 4: Immunisation scheme 3: Gr. HV4.8 – HV4.10 as well as HV4.17 – HV4.19

SEQUENCE LISTING

<160> NUMBER OF SEQ ID NOS: 3

<210> SEQ ID NO 1
<211> LENGTH: 1881
<212> TYPE: DNA
<213> ORGANISM: Artificial Sequence
<220> FEATURE:
<223> OTHER INFORMATION: Description of Artificial Sequence: recombinant
      nucleic acid molecule
<220> FEATURE:
<223> OTHER INFORMATION: CDS comprising a phagolysosomal domain
      (211-1722 nt) and a stop codon (1879-1881)

<400> SEQUENCE: 1

| | |
|---|---|
| atgacagacg tgagccgaaa gattcgagct tggggacgcc gattgatgat cggcacggca | 60 |
| gcggctgtag tccttccggg cctggtgggg cttgccggcg gagcggcaac cgcgggcgcg | 120 |
| ttctcccggc cggggctgcc ggtcgagtac ctgcagtctg caaagcaatc cgctgcaaat | 180 |
| aaattgcact cagcaggaca aagcacgaaa gatgcatctg cattcaataa agaaaattca | 240 |
| atttcatcca tggcaccacc agcatctccg cctgcaagtc ctaagacgcc aatcgaaaag | 300 |
| aaacacgcgg atgaaatcga taagtatata caaggattgg attacaataa aaacaatgta | 360 |
| ttagtatacc acggagatgc agtgacaaat gtgccgccaa gaaaaggtta caagatgga | 420 |
| aatgaatata ttgttgtgga gaaaagaag aaatccatca atcaaaataa tgcagacatt | 480 |
| caagttgtga atgcaatttc gagcctaacc tatccaggtg ctctcgtaaa agcgaattcg | 540 |
| gaattagtag aaaatcaacc agatgttctc cctgtaaaac gtgattcatt aacactcagc | 600 |
| attgatttgc caggtatgac taatcaagac aataaaatcg ttgtaaaaaa tgccactaaa | 660 |
| tcaaacgtta caacgcagt aaatacatta gtggaaagat ggaatgaaaa atatgctcaa | 720 |
| gcttatccaa atgtaagtgc aaaaattgat tatgatgacg aaatggctta cagtgaatca | 780 |
| caattaattg cgaaatttgg tacagcattt aaagctgtaa ataatagctt gaatgtaaac | 840 |
| ttcggcgcaa tcagtgaagg gaaaatgcaa gaagaagtca ttagttttaa acaaatttac | 900 |
| tataacgtga atgttaatga acctacaaga ccttccagat ttttcggcaa agctgttact | 960 |
| aaagagcagt tgcaagcgct tggagtgaat gcagaaaatc ctcctgcata tatctcaagt | 1020 |
| gtggcgtatg ccgtcaagt ttatttgaaa ttatcaacta attcccatag tactaaagta | 1080 |
| aaagctgctt ttgatgctgc cgtaagcgga aaatctgtct caggtgatgt agaactaaca | 1140 |
| aatatcatca aaattcttc cttcaaagcc gtaatttacg gaggttccgc aaaagatgaa | 1200 |
| gttcaaatca tcgacggcaa cctcggagac ttacgcgata ttttgaaaaa aggcgctact | 1260 |
| tttaatcgag aaacaccagg agttcccatt gcttatacaa caaacttcct aaaagacaat | 1320 |
| gaattagctg ttattaaaaa caactcagaa tatattgaaa caacttcaaa agcttataca | 1380 |
| gatggaaaaa ttaacatcga tcactctgga ggatacgttg ctcaattcaa catttcttgg | 1440 |
| gatgaagtaa attatgatcc tgaaggtaac gaaattgttc aacataaaaa ctggagcgaa | 1500 |
| aacaataaaa gcaagctagc tcatttcaca tcgtccatct atttgccagg taacgcgaga | 1560 |
| aatattaatg tttacgctaa agaatgcact ggtttagctt gggaatggtg agaacggta | 1620 |
| attgatgacc ggaacttacc acttgtgaaa aatagaaata tctccatctg gggcaccacg | 1680 |
| ctttatccga aatatagtaa taagtagat aatccaatcg aatatgcatt agcctatgga | 1740 |
| agtcagggtg atcttaatcc attaattaat gaaatcagca aaatcatttc agctgcagtt | 1800 |
| cttttcctctt taacatcgaa gctacctgca gagttcgtta ggcgcggatc cggaattcga | 1860 |
| agcttatcga tgtcgacgta g | 1881 |

<210> SEQ ID NO 2
<211> LENGTH: 626
<212> TYPE: PRT
<213> ORGANISM: Artificial Sequence
<220> FEATURE:
<223> OTHER INFORMATION: Description of Artificial Sequence: corresponding amino acid sequence of nucleic acid sequence 1

<400> SEQUENCE: 2

```
Met Thr Asp Val Ser Arg Lys Ile Arg Ala Trp Gly Arg Arg Leu Met
 1               5                  10                  15

Ile Gly Thr Ala Ala Ala Val Val Leu Pro Gly Leu Val Gly Leu Ala
                20                  25                  30

Gly Gly Ala Ala Thr Ala Gly Ala Phe Ser Arg Pro Gly Leu Pro Val
            35                  40                  45

Glu Tyr Leu Gln Ser Ala Lys Gln Ser Ala Ala Asn Lys Leu His Ser
    50                  55                  60

Ala Gly Gln Ser Thr Lys Asp Ala Ser Ala Phe Asn Lys Glu Asn Ser
65                  70                  75                  80

Ile Ser Ser Met Ala Pro Pro Ala Ser Pro Ala Ser Pro Lys Thr
                85                  90                  95

Pro Ile Glu Lys Lys His Ala Asp Glu Ile Asp Lys Tyr Ile Gln Gly
            100                 105                 110

Leu Asp Tyr Asn Lys Asn Asn Val Leu Val Tyr His Gly Asp Ala Val
        115                 120                 125

Thr Asn Val Pro Pro Arg Lys Gly Tyr Lys Asp Gly Asn Glu Tyr Ile
    130                 135                 140

Val Val Glu Lys Lys Lys Lys Ser Ile Asn Gln Asn Asn Ala Asp Ile
145                 150                 155                 160

Gln Val Val Asn Ala Ile Ser Ser Leu Thr Tyr Pro Gly Ala Leu Val
                165                 170                 175

Lys Ala Asn Ser Glu Leu Val Glu Asn Gln Pro Asp Val Leu Pro Val
            180                 185                 190

Lys Arg Asp Ser Leu Thr Leu Ser Ile Asp Leu Pro Gly Met Thr Asn
        195                 200                 205

Gln Asp Asn Lys Ile Val Val Lys Asn Ala Thr Lys Ser Asn Val Asn
    210                 215                 220

Asn Ala Val Asn Thr Leu Val Glu Arg Trp Asn Glu Lys Tyr Ala Gln
225                 230                 235                 240

Ala Tyr Pro Asn Val Ser Ala Lys Ile Asp Tyr Asp Asp Glu Met Ala
                245                 250                 255

Tyr Ser Glu Ser Gln Leu Ile Ala Lys Phe Gly Thr Ala Phe Lys Ala
            260                 265                 270

Val Asn Asn Ser Leu Asn Val Asn Phe Gly Ala Ile Ser Glu Gly Lys
        275                 280                 285

Met Gln Glu Glu Val Ile Ser Phe Lys Gln Ile Tyr Tyr Asn Val Asn
    290                 295                 300

Val Asn Glu Pro Thr Arg Pro Ser Arg Phe Phe Gly Lys Ala Val Thr
305                 310                 315                 320

Lys Glu Gln Leu Gln Ala Leu Gly Val Asn Ala Glu Asn Pro Pro Ala
                325                 330                 335

Tyr Ile Ser Ser Val Ala Tyr Gly Arg Gln Val Tyr Leu Lys Leu Ser
            340                 345                 350

Thr Asn Ser His Ser Thr Lys Val Lys Ala Ala Phe Asp Ala Ala Val
```

```
                    355                 360                 365
Ser Gly Lys Ser Val Ser Gly Asp Val Glu Leu Thr Asn Ile Ile Lys
    370                 375                 380

Asn Ser Ser Phe Lys Ala Val Ile Tyr Gly Gly Ser Ala Lys Asp Glu
385                 390                 395                 400

Val Gln Ile Ile Asp Gly Asn Leu Gly Asp Leu Arg Asp Ile Leu Lys
                405                 410                 415

Lys Gly Ala Thr Phe Asn Arg Glu Thr Pro Gly Val Pro Ile Ala Tyr
            420                 425                 430

Thr Thr Asn Phe Leu Lys Asp Asn Glu Leu Ala Val Ile Lys Asn Asn
        435                 440                 445

Ser Glu Tyr Ile Glu Thr Thr Ser Lys Ala Tyr Thr Asp Gly Lys Ile
    450                 455                 460

Asn Ile Asp His Ser Gly Gly Tyr Val Ala Gln Phe Asn Ile Ser Trp
465                 470                 475                 480

Asp Glu Val Asn Tyr Asp Pro Glu Gly Asn Glu Ile Val Gln His Lys
                485                 490                 495

Asn Trp Ser Glu Asn Asn Lys Ser Lys Leu Ala His Phe Thr Ser Ser
            500                 505                 510

Ile Tyr Leu Pro Gly Asn Ala Arg Asn Ile Asn Val Tyr Ala Lys Glu
        515                 520                 525

Cys Thr Gly Leu Ala Trp Glu Trp Trp Arg Thr Val Ile Asp Asp Arg
    530                 535                 540

Asn Leu Pro Leu Val Lys Asn Arg Asn Ile Ser Ile Trp Gly Thr Thr
545                 550                 555                 560

Leu Tyr Pro Lys Tyr Ser Asn Lys Val Asp Asn Pro Ile Glu Tyr Ala
                565                 570                 575

Leu Ala Tyr Gly Ser Gln Gly Asp Leu Asn Pro Leu Ile Asn Glu Ile
            580                 585                 590

Ser Lys Ile Ile Ser Ala Ala Val Leu Ser Ser Leu Thr Ser Lys Leu
        595                 600                 605

Pro Ala Glu Phe Val Arg Arg Gly Ser Gly Ile Arg Ser Leu Ser Met
    610                 615                 620

Ser Thr
625

<210> SEQ ID NO 3
<211> LENGTH: 9
<212> TYPE: PRT
<213> ORGANISM: Artificial
<220> FEATURE:
<223> OTHER INFORMATION: Synthetic peptide

<400> SEQUENCE: 1

Ser Ile Ile Asn Phe Glu Lys Glu Leu
  1               5
```

COMBINATION OF A BACTERIAL CELL AND A BIOLOGICALLY ACTIVE AGENT

FIELD OF THE INVENTION

The present invention is related to a combination comprising at least two constituents, the use of such combination as a pharmaceutical composition, its use for the manufacture of a medicament, methods for the treatment of a patient using such combination and a method for manufacturing such combination. In more particular embodiments, the combinations are of use as vaccines.

BACKGROUND

Modern molecular medicine strongly focuses on the use of immunogenic compounds or compounds modulating the immune system of a patient for the treatment of such patient. Respective diseases are, among others, tumors and infectious diseases.

In both cases, antigenic compounds, i.e. compounds which are suitable to elicit an immune response or to strengthen an immune response are administered to the patient's body. The usefulness of the respective compounds is, however, in many cases limited which requires a boost of the immune response so as to reach a clinically relevant level of efficiency and efficacy. Such boost can be performed by repeatedly administering the respective agent, or by using an adjuvant.

The prior art provides for several adjuvants such as mineral oils, inactivated mycobacteria, aluminium compounds and the like.

The adjuvants known in the art, however, are not always performing in a manner sufficient to meet the medical needs, in particular in connection with new treatment regimens such as the use of cytokine expressing cells as, for example, described in international patent application PCT/US94/01631.

The problem underlying the present invention is thus to provide compositions, more particularly pharmaceutical compositions, which comprise at least a first constituent and a second constituent, whereby the first constituent is an adjuvant and the second constituent is a biologically active agent.

SUMMARY

This problem is solved in a first aspect by a combination comprising a first constituent and a second constituent, wherein the first constituent is a bacterial cell which comprises at least one recombinant nucleic acid molecule encoding a phagolysosomal escape peptide or polypeptide; and wherein the second constituent is a biologically active agent. In more particular embodiments, the biologically active agent is an antigenic cell, fusion protein or immunomolecule that, when co-administered with the first constituent, is effective to induce an immune response in a mammal against the biologically active agent and/or cells or pathogens associated with the biologically active agent.

In an embodiment the bacterial cell is urease-deficient.

In a further embodiment the bacterial cell is a *Mycobacterium* cell.

In a preferred embodiment the cell is a *Mycobacterium bovis* cell.

In a preferred embodiment at least one cellular urease subunit encoding nucleic acid of the bacterial cell is inactivated.

In a more preferred embodiment at least the bacterial urease C subunit-encoding sequence is inactivated.

In an embodiment the phagolysosomal escape domain is a *Listeria* phagolysosomal escape domain.

In an embodiment the phagolysosomal domain is encoded by a nucleic acid molecule selected from the group comprising
  a) a nucleotide sequence comprising nucleotide 211-1,722 as shown in SEQ. ID. NO. 1;
  b) a nucleotide sequence which encodes for the same amino acid sequence as the sequence from a); and
  c) a nucleotide sequence hybridising under stringent conditions with the sequence from a) or b).

In an embodiment the bacterial cell comprises at least one recombinant nucleic acid molecule encoding a peptide or polypeptide capable of eliciting an immune response in a mammal.

In a more preferred embodiment the peptide or polypeptide is selected from autoantigens, tumor antigens, virus antigens, parasite antigens, bacterial antigens and immunogenic fragments thereof.

In a further preferred embodiment the peptide or polypeptide is part of a fusion polypeptide.

In an embodiment the fusion polypeptide comprises
  a) at least one domain from a polypeptide, wherein the polypeptide domain is capable of eliciting an immune response in a mammal, and
  b) a phagolysosomal escape domain.

In a preferred embodiment the polypeptide is the polypeptide as defined in claim 9 or part thereof.

In a further preferred embodiment the phagolysosomal escape domain is a domain of the phagolysosomal escape domain as defined in any of claims 1 to 11.

In a preferred embodiment the bacterial cell is rBCG:Hly or rBCGΔureC:Hly.

In an embodiment the biologically active agent is a eukaryotic cell and more preferably a genetically manipulated eukaryotic cell which expresses a cytokine.

In a preferred embodiment the cytokine is selected from the group comprising interleukin-2, interleukin-4, interleukin-12 and interferon-gamma.

In a more preferred embodiment the cell co-expresses two or more cytokines.

In a still more preferred embodiment the cell co-expresses IL-2 and interferon-gamma.

In a preferred embodiment the cell is autologous relative to a subject to whom the cell and/or the composition is administered or is to be administered.

In a preferred alternative embodiment the cell is allogeneic relative to a subject to whom the cell and/or the composition is administered or is to be administered.

In a preferred embodiment the cell is selected from the group comprising non-professional antigen presenting cells, professional antigen presenting cells, tumor cells and dendritic cells.

In a more preferred embodiment the tumor cell is a cell of an immunogenic tumor and wherein the tumor cells are preferably selected from the group comprising melanoma cells, renal carcinoma cells, breast tumor cells, brain tumor cells, prostate tumor cells, non-small cell lung cancer, colon carcinoma, head and neck squamous tumor.

In a preferred embodiment the cell is an allogeneic cell and is HLA class I matched.

In another preferred embodiment the cell expresses another immunomolecule selected from the group comprising a cytokine, an adhesion molecule, a co-stimulatory factor, a tumor-associated antigen, a tumor specific antigen and a parasite antigen.

In a more preferred embodiment the parasite antigen is gp190/MSP1 protein of *Plasmodium*, preferably *Plasmodium falciparum*, or a fragment thereof capable of eliciting an immune response in a mammal.

In a preferred embodiment the biologically active agent is the gp190/MSP1 protein of *Plasmodium*, preferably *Plasmodium falciparum*, or a fragment thereof capable of eliciting an immune response in a mammal.

In an embodiment the biologically active agent is human cytomegalovirus.

In a preferred embodiment the biologically active agent is a viral particle or a multitude thereof, preferably released after infection of mammalian cells by human cytomegalovirus, whereby the particles (a) are surrounded by a lipid membrane in which viral glycoproteins are embedded, and (b) contain neither viral DNA nor capsids.

In a preferred embodiment the particles contain a fusion protein comprising one or more parts of the T-cell antigen pp65 (UL83) and one or more parts of one or more proteins which are not pp65.

In a preferred embodiment the T-cell antigen pp65 is fused to one or more parts of a glycoprotein of the human cytomegalovirus, whereby the glycoprotein is selected from the group comprising the HCMV glycoprotein gH, HCMV protein $IE_1$ (ppUL123), and the HCMV glycoprotein gB.

In a preferred embodiment the T-cell antigen is fused to one or more parts of a protein which is part of a human pathogen other than HCMV.

In a preferred embodiment the pathogen is selected from the group comprising HIV-1, HBV, HCV and influenza.

In a preferred embodiment the particle(s) contain(s) parts of at least two glycoproteins which are variants of a particular glycoprotein from different HCMV strains.

In a more preferred embodiment one of the two variants of the particular HCMV glycoprotein is the variant of the HCMV Towne strain, and the other is the variant of the HCMV Ad169 strain.

In a preferred embodiment the mammalian cells are fibroblasts, preferably foreskin fibroblasts.

In a preferred embodiment the particle is a dense body.

In a preferred embodiment the biologically active agent is a dense body, preferably a dense body of HCMV, or a dense body as defined herein.

In an embodiment the biologically active agent is an antigen from *Mycobacterium*, preferably *Mycobacterium* ssp.

In a preferred embodiment the *Mycobacterium* is selected from the group comprising *M. tuberculosis, M. bovis, M. canettii, M. africanum* and *M. paratuberculosis*.

In a preferred embodiment the antigen is antigen 85.

In a second aspect the problem underlying the present invention is solved by a composition, preferably a pharmaceutical composition comprising a combination according to the first aspect of the present invention and optionally a pharmaceutically acceptable carrier.

In a third aspect the problem underlying the present invention is solved by the use of a combination according to the first aspect of the present invention or a combination according to the second aspect of the present invention or each of the constituents of such combination for the manufacture of a medicament.

In an embodiment the medicament is for the prevention and/or treatment of a disease selected from the group comprising cancer and infectious diseases.

It will be acknowledged by the ones skilled in the art that the composition of the present invention and its constituents either alone or in combination may preferably also be used for the prevention of a disease. This is in preferred embodiments based on the fact that the first constituent of the combination according to the present invention is suitable to elicit an immune response and more particularly a specific immune response which allows to provide a respective human or animal body to fight the disease prior to a manifestation of the disease and more specifically prior to a clinically or medically relevant manifestation of the diseases.

In a preferred embodiment the cancer is an immunogenic tumor and wherein the tumor is preferably is selected from the group comprising prostate cancer, melanoma, renal carcinoma, breast tumor, brain tumors, non-small lung cancer, colon carcinoma, and head and neck squamous tumor.

In an alternative embodiment the infectious disease is Malaria.

In a preferred embodiment the biologically active agent is gp190MSP1 protein of *Plasmodium* or a fragment thereof capable of eliciting an immune response in a mammal.

In an alternative embodiment the infectious disease is HCMV infection, preferably human HCMV infection. In a preferred embodiment, the biologically active agent is a dense body as disclosed herein.

In an alternative embodiment the infectious disease is tuberculosis. In a preferred the biologically active agent is an antigen from *Mycobacterium*, preferably *Mycobacterium* ssp. More preferably, the *Mycobacterium* is selected from the group comprising *M. tuberculosis, M. bovis, M. canettii, M. africanum* and *M. paratuberculosis*. Even more preferably, the antigen is antigen 85.

In a fourth aspect the problem underlying the present invention is solved by the use of a combination according to the first aspect of the present invention or each of the constituents of such combination for the manufacture of a vaccine.

In a fifth aspect the problem underlying the present invention is solved by a method for the treatment of a patient suffering from a disease and in need of such treatment, comprising administering a combination according to the first aspect of the present invention or a pharmaceutical combination according to the second aspect of the present invention.

In a sixth aspect the problem underlying the present invention is solved by a method for the manufacture of a pharmaceutical combination, preferably a pharmaceutical composition according to the second aspect of the present invention, comprising the steps of providing as a first constituent a bacterial cell which comprises at least one recombinant nucleic acid molecule encoding a phagolysosomal escape peptide or polypeptide;

providing as a second constituent a biologically active agent; and formulating the first constituent and the second constituent into a pharmaceutical composition.

In a seventh aspect the problem underlying the present invention is solved by a method for the manufacture of a pharmaceutical combination, preferably a pharmaceutical composition according to the second aspect of the present invention comprising the steps of providing as a first constituent a bacterial cell which comprises at least one recombinant nucleic acid molecule encoding a phagolysosomal escape peptide or polypeptide;

providing as a second constituent a biologically active agent; and formulating the first and the second constituent separately.

In an embodiment, the formulated first constituent and the formulated second constituent are packed in a single package.

Alternatively, the formulated first constituent and the formulated second constituent are packed in separated packages.

In a more preferred embodiment, the packages are single dosage units or comprise multiple single dosage units.

DETAILED DESCRIPTION

The present inventors have surprisingly found that a bacterial cell which may either be a Gram-positive or a Gram-negative bacterial cell which expresses a phagolysosomal escape peptide or polypeptide is a particularly useful adjuvant which can be used in combination with a biologically active agent. More particularly, the present inventors have recognised that *Mycobacterium bovis*, preferably *Mycobacterium bovis* Bacille Calmette-Guérin (BCG) and more preferably *Mycobacterium* such as BCG encoding or expressing a phagolysosomal escape peptide or polypeptide is a suitable means to elicit an immune response or to strengthen the immune response particularly mediated when using biologically active agents and more particularly other immune eliciting biologically active agents. A particularly preferred type of immune response eliciting biologically active agents is a cell expressing at least one cytokine or a parasite antigen, or a tumor or parasite antigen or a virus antigen.

Without wishing to be bound by any theory, the present inventors are of the opinion that such phagolysosomal escape peptide or polypeptide allows that any antigens derived from the bacterial cell or from the biologically active agent and suitable to elicit an immune response, are more efficient in doing so once such phagolysosomal escape peptide is available. In other words, by allowing the antigens created upon the entrapment of the bacterial cell into the phagolysosomes, to escape therefrom and thus being presented to the immune system increases the accessibility of BCG specific antigens and thus creating the superior adjuvant effect used in connection with the present invention.

This kind of delivery of peptides into the MHC class I presentation pathway may potentiate the already existing BCG-specific immune response and its adjuvant activity.

The adjuvant effect of BCG and more particularly of BCG or any microorganism, preferably any *Mycobacterium* organism, which encodes or expresses a phagolysosomal escape peptide or polypeptide is a further surprising finding of the present inventors which can preferably be made use of when such adjuvant effect causing microorganism is combined or co-administered with a further or second biologically active agent. Unlike other adjuvants which stimulate a TH2 immune response, the afore-described adjuvant, i.e. microrganism, can be used to elicit a TH1 immune response. Such TH1 immune response is useful insofar as it induces a cellular immune response. Therefore, in a further aspect, the invention is related to the use of a microorganism which codes for and/or expresses a phagolysosomal escape peptide, whereby the microorganism is preferably BCG and more preferably BCG as described herein and most preferably a ureC-deficient BCG, as an adjuvant.

Even more surprisingly the present inventors have found that a microorganism, preferably BCG or its derivatives, which code for and/or expresses a phagolysosomal escape peptide and more preferably BCG as described herein in its various embodiments, including but not limited to rBCG:Hly and most preferably a ureC-deficient BCG such as BCG: rBCG ΔureC:Hly and derivatives thereof are superior to BCG without a phagolysosomal escape peptide in so far that they are capable of inducing a pronounced CD8 response which is specific for the respective microorganism such as *Mycobacterium*, and, additionally, also a pronounced CD8 response which is specific for the antigen represented by or given as the biologically active agent as disclosed and/or defined herein. In other words, the microorganism used as or referred to as the first constituent herein, in this embodiment, i.e. comprising a phagolysosomal escape peptide and more preferably additionally being ureC negative, is not limited to eliciting the microorganism-specific CD8 immune response in contrast to what the one skilled in the art would have expected.

In a preferred embodiment, such phagolysosomal escape peptide or polypeptide is the phagolysosomal escape polypeptide of *L. monocytogenes*, listeriolysin (Hly). Listeriolysin is a pore-forming sulfhydryl activated cytolysin and is responsible for the release of *L. monocytogenes* microorganisms from phagolysosomal vacuoles into the cytosol of host cells. This escape function can be transferred to various bacterial cells such as *Bacillus subtilis*, attenuated *Salmonella* ssp. strains and *Mycobacterium* as well, as described in international patent application PCT/EP2004/004345. Also, international patent application WO 99/101496 discloses recombinant *Mycobacterium bovis* strains that secrete biologically active listeriolysin fusion proteins. The bacterial cell forming the first constituent of the composition according to the present invention thus exhibits a pore formation mechanism for perforating endosomal membranes leading to superior immuno protectivity.

It will be acknowledged by the ones skilled in the art that there are several phagolysosomal escape domains, whereby the *listeria* phagolysosomal escape domain which is, for example, described in U.S. Pat. No. 5,733,151, is preferred. More preferably, the phagolysosomal escape domain is derived from the organism *L. monocytogenes*, most preferably, the phagolysosomal escape domain is encoded by a nucleic acid molecule selected from a) a nucleotide sequence comprising nucleotides 211-1,722 as shown in SEQ. ID. NO. 1, b) a nucleotide sequence which encodes for the same amino acid sequence as the sequence from a) and c) a nucleotide sequence hybridising under stringent conditions with the sequence from a) or b). Other phagolysosomal escape polypeptides which can be used for such purpose are, among others, hemolysin (Perfringolysin) from *Clostridium perfringens* (O'Brien D K, et al. Infect Immun. 2004 September; 72(9):5204-15); hemolysine from *Vibrio*, more particularly *Vibrio vulnificus* (Lee S E et al., Biochem BiophysRes Commun. 2004 Nov. 5; 324(1): 86-91); hemolysine/cytolysine from group B *streptococcus* (Liu G Y et al., Proc Natl Acad Sci USA. 2004 Oct. 5; 101(40):14491-14496. Epub 2004 Sep. 20); hemolysine BL from *Bacillus*, more particularly *Bacillus cereus* (Moravek M et al., FEMS Microbiol Lett. 2004 Sep. 1; 238(1):107-13); hemolysine from *Bordetella*, more particularly *Bordetella pertusis* (Bassinet L et al., Infect Immun. 2004 September; 72(9):5530-3); hemolysine from *Escherichia coli* (Wyborn N R et al., Microbiology. 2004 May; 150(Pt 5):1495-505) and hemolysine from *Shigella* (Sharma K et al., Microbios. 2001; 106(413):31-8).

Apart from the nucleotide sequence depicted in SEQ ID No. 1 the present invention also comprises nucleic acid sequences hybridizing therewith. In the present invention the term "hybridization" is used as defined in Sambrook et al. (Molecular Cloning. A laboratory manual, Cold Spring Harbor Laboratory Press (1989), 1.101-1.104). In accordance with the present invention the term "hybridization" is used if a positive hybridization signal can still be observed after washing for one hour with 1×SSC and 0.1% SDS at 55° C., preferably at 62° C. and more preferably at 68° C. A sequence hybridizing with a nucleotide sequence as per SEQ ID No. 1 under such washing conditions is a phagolysosomal escape domain encoding nucleotide sequence preferred by the present invention.

A nucleotide sequence encoding a phagolysosomal escape domain as described above may be directly obtained from a *Listeria* organism or from any recombinant source, e.g. a recombinant *E. coli* cell containing the corresponding *Listeria* nucleic acid molecule or a variant thereof as described above.

It is to be acknowledged that such bacterial cell comprising at least one recombinant nucleic acid molecule encoding a phagolysosomal escape peptide and more particularly such bacterial cell being a *Mycobacterium* cell comprising Hly is particularly preferred for the composition according to the present invention. In a further preferred embodiment, said bacterial cell is furthermore urease deficient, more particularly ureC deficient. Such organism is also referred to as BCG: rBCG ΔureC:Hly or as BKG.

*Mycobacterium* and more particularly *Mycobacterium bovis* Bacille Calmette-Guérin (BCG) has been widely used as viable vaccine for the prevention of tuberculosis, although its efficacy is still questionable. Nevertheless, agreement exists that BCG can protect against, or at least ameliorate, severe forms of systemic *tuberculosis* in children.

However, new forms of BCG have now been developed. The present inventors have found that these novel forms of BCG are particularly useful as adjuvants when administered together with a biologically active agent and may thus be used as the first constituent of the combination according to the present invention.

The bacterial cell which is used as the first constituent of the combination according to the present invention is preferably urease deficient. This trait results in an increased safety profile as, because of the urea deficiency, the mycobacterial cell would not survive in an environment where such enzymatic activity is required, such as in the phagolysosome.

The urease-deficiency may be achieved by partially or completely inactivating one or several cellular nucleic acid molecules which code for a urease subunit, particularly ureA coding for urease subunit A, ureB coding for urease subunit B and/or ureC coding for urease subunit C. The sequences of ureA, ureB and ureC in *Mycobacteria*, particularly *M. bovis* and *M. tuberculosis* and the proteins encoded thereby, are described by Reyrat et al. (1995) and Clemens et al. (1995), which are incorporated herein by reference.

Preferably, the urease-deficient bacterial strain is obtained by deletions and/or insertions of one or several nucleotides in urease subunit-coding nucleic acid sequences and/or the expression control sequences. Deletions and/or insertions may be generated by homologous recombination, transposon insertion or other suitable methods.

In an especially preferred embodiment the ureC sequence is inactivated, e.g. by constructing a suicide vector containing a ureC gene disrupted by a selection marker gene, transforming the target cell with the vector and screening for selection marker-positive cells having a urease negative phenotype as described by Reyrat et al. (supra).

According to the present invention, various species from *Mycobacterium* can be used as the bacterial cell forming the first constituent of the composition according to the present invention, namely *M. bovis, M. tuberculosis, M. microti, M. smegmatis, M. canettii, M. marinum* or *M. fortuitum*. It is also within the present invention that other microorganisms, preferably intracellular microorganisms, may be used which exhibit one or both of the aforementioned characteristics, namely to code or express a phagolysosomal escape peptide or polypeptide, and to be urease-negative, more particularly ureC-negative.

In a further embodiment, the respective bacterial cell is attenuated. In a more preferred embodiment, the bacterial cell is attenuated but is still alive and is more particularly suitable to elicit a TH1 response.

In a more preferred embodiment the respective bacterial cell is a live bacterial cell.

In a further embodiment, the bacterial cell further comprises at least one recombinant nucleic acid molecule encoding a peptide or polypeptide capable of eliciting an immune response in a mammal. As used herein, the term eliciting an immune response in a mammal means that upon exposure of such peptide or polypeptide to the immune system of a mammal or part thereof, an immune response can be created which is a B cell-mediated immune response. Alternatively, however, the immune response is a T-cell mediated immune response, more preferably a MHC class 1-restricted CD8 T cell response.

More preferably, such peptide or polypeptide is selected from the group comprising auto antigens, tumor antigens, virus antigens, parasite antigens, bacterial antigens and immunogenic fragments thereof. Preferably, an immunogenic fragment is part of such antigen which is still capable of eliciting an immune response. A particular preferred antigen is gp190/MSP1 protein of *Plasmodium*, as described in more detail herein. A further particularly preferred virus antigen are dense bodies of HCMV as described in more detail herein. A still further antigen is antigens suitable to elicit an immune response against tuberculosis and more specifically against *Mycobacterium tuberculosis, M. bovis, M. canettii, M. africanum* and *M. paratuberculosis*. A particularly preferred antigen is antigen 85. Such antigen is, in a preferred embodiment, the second constituent.

It will be acknowledged by the ones skilled in the art that whenever it is referred to an antigen herein, this term also comprises fragments or mutated forms thereof. Fragments and mutated forms thereof are regarded as the respective antigen as long as such mutated form or fragment thereof exhibits at least one characteristic of the full-length or wild-type antigen. Preferably, such characteristic is its capability to elicit an immune response, more preferably an immune response when used together or in combination with the first constituent or an adjuvant as described herein. In an even more preferred embodiment such immune response is a specific CD8 immune response. This applies also to polypeptides and proteins, respectively.

It will be further acknowledged by the ones skilled in the art that whenever it is referred to a nucleic acid and a nucleic acid coding for a polypeptide or protein, respectively, the term is also to comprise those nucleic acids which code for the polypeptide or protein, optionally being a fragment or a mutated form thereof as preferably being defined herein, in view of the degeneracy of the genetic code or in view of the need to adapt the sequence to the codon usage of the respective host or production organism.

The term that a polypeptide, protein or antigen is derived from an organism preferably means that the amino acid sequence of the respective polypeptide, protein or antigen is the one of the respective organism, whereby the sequence and thus also the corresponding nucleic acid coding therefore can be fragments and mutated forms thereof.

It is to be acknowledged that the peptide or polypeptide capable of eliciting an immune response in a mammal can be the second constituent of the composition. It is within the present invention that the peptide or polypeptide is part of a fusion polypeptide. Preferably, such fusion polypeptide comprises the peptide or polypeptide capable of eliciting an immune response in a mammal or a domain thereof still having this trait, and the fusion polypeptide further comprising a phagolysosomal escape domain, preferably a phagolysosomal escape domain as described above in connection with the embodiments of the first constituent of the present invention. The domain of a polypeptide which is capable of eliciting an immune response in a mammal may be, in case such peptide is a bacterial antigen, derived from a microorganism, preferably from the genus *Mycobacterium* and more preferably from *Mycobacterium tuberculosis* or from *Mycobacterium bovis*. This domain has a length of at least 6, preferably of at least 8 amino acids. The immunogenic domain is preferably a portion of a native *Mycobacterium* polypeptide. However, also modified immunogenic domains which can be derived from a native immunogenic domain by substituting, deleting and/or adding one or several amino acids, is within the scope of the present invention. In a preferred embodiment the domain is a domain of gp190/MSP 1 protein of *Plasmodium*.

In an embodiment fusion protein is encoded by a recombinant nucleic acid molecule, namely nucleic acid molecule according to SEQ ID No. 1. This nucleic acid molecule comprises a signal peptide coding sequence, (nucleotide 1 to 120), a sequence coding for a immunogenic domain (nucleotide 112 to 153), a peptide linker coding sequence (nucleotide 154 to 210), a sequence coding for a phagolysosomal domain (nucleotide 211 to 1722), a further peptide linker coding sequence (nucleotide 1723 to 1800) and a sequence coding for a random peptide (nucleotide 1801 to 1870). The corresponding amino acid sequence is shown in SEQ ID No. 2.

In a particularly preferred embodiment, more particularly when the first constituent is either rBCG:Hly or rBCGΔureC: Hly, the second constituent is a biologically active agent and more particularly a genetically manipulated cell. Preferably, the genetically manipulated cell is a eukaryotic cell. More preferably, such genetically manipulated cell expresses at least one cytokine. A cytokine as used herein is a secreted protein which influences the behaviour and characteristics of other cells. Preferred cytokines are interleukins, chemokines, lymphokines, monokines and growth factors. Particularly preferred cytokines are interleukins and interferons, whereby preferred interleukins are interleukin-2, interleukin-4, interleukin-12, preferably interleukin-2, and interferon is preferably interferon-alpha, interferon-beta or interferon-gamma, more preferably interferon-gamma.

As preferably used herein, a genetically manipulated cell is a cell modified with regard to the genetic make-up which is present in the cell by inserting exogenous genetic material. Such modification of the genetic make-up comprises the introduction of genetic material not yet present in the cell, so as to be a truly foreign nucleic acid, or to activate a part of the endogenous genetic material, whereby such endogenous genetic material is not present or active without said exogenous genetic material present, whereby exogenous genetic material is not necessarily a genetic material, but can be any material active insofar. The methods to achieve such modification are well-known in the art. For example, exogenous DNA material can be introduced into the cell by calcium phosphate precipitation technology, viral vector technology, electroporation, lipofection, viral vector systems such as adeno-associated virus systems, microinjection or biolistic approaches. The result of such genetic manipulation is that the genetically manipulated cell would be able to express certain gene product which was not expressed before.

The present inventors have found that the co-expression of the interleukins, and more particularly interleukin-2, and interferon-gamma, in combination with the bacterial cell described as the first constituent of the combination according to the present invention, provides for a very effective way to increase the immune response of an organism, more particularly TH1 response. The particular cell may be chosen from a variety of cells such as non-professional antigen presenting cells, professional antigen presenting cells, tumor cells and dendritic cells. Among these cell types, tumor cells are particularly preferred. Upon administration of such tumor cells, cancer patients into which such tumor cells have been introduced, experience an increased effect on the efficacy of tumor vaccination approaches. Preferably, the cells used for such vaccination process are taken from the same or a similar tumor entity as the tumor to be treated using the combination according to the present invention. The beneficial effects of using genetically manipulated cells which are, among others, described in international patent application WO 94/18995, are thus further increased by using the bacterial cell as forming the first constituent of the combination according to the present invention.

It is within the present invention that the professional antigen presenting cell is a dendritic cell which is then either used as a biologically active agent as defined herein, or is a further component of the biologically active agent, whereby preferably in such embodiment the biologically active agent is a genetically manipulated cell, more preferably a cytokine expressing cell as described herein, whereby the cell even more preferably co-expresses two cytokines and most preferably interleukin-2 and interferon-gamma. The dendritic cells are preferably loaded with antigens from a tumor, whereby the tumor is the one for the treatment of which the dendritic cell is used, preferably in combination with the adjuvants as described herein and/or the combination of an adjuvants and a biologically active agent such as, for example, said cytokines co-expressing cells. The loading of the dendritic cells is known to the one skilled in the art and, for example, described in Vari and Hart ((2004), Cytotherapy: 6(2): 111-121.). Such dendritic cells either alone or in combination with any of the adjuvants described herein, particularly BCG and BKG, or any combination of first and second constituent described herein is preferably used for the treatment of any of the diseases described herein. Preferably such disease is any tumor disease described herein.

Preferred tumors and cancers, respectively, which can be addressed using this kind of approach are in particular immunogenic tumors or cancers such as, among others, melanoma, renal cancer, breast tumor, brain tumor, prostate tumor, non-small lung cancer, colon carcinoma, and head and neck squamous tumor.

The expression of a cytokine and more particularly co-expression of interleukin-2 and interferon-gamma allows for an increased efficacy of the tumor antigens presented by the genetically manipulated cell. The improvement in the anti-tumour response is brought about by two different mechanisms which operate towards the same direction. On the afferent side, IFNγ secretion increases the expression of MHC and adhesion molecules at the cell surface leading to a better presentation of tumour specific antigens to $CD8^+$ T-cells by MHC 1 molecules and thus to a better recognition of tumour cells by T-cells. On the efferent side, IL-2 secretion in close proximity to tumour cells increases the activity of $CD8^+$ T-cells. Insofar, preferably the genetically manipulated cell expressing at least one cytokine is in a preferred embodiment at least to a certain extent related to the tumor entity for the treatment of which it is used. Of course, it will be understood that other cell lines can be used insofar, whereby it is more preferred that said cell in addition to being genetically manipulated as described herein, also expresses certain antigens characteristic of the tumor entity to be thus treated.

It will be acknowledged by the ones skilled in the art that, in principle, the genetically manipulated cell can be an autologous cell. This means that a cell is taken from a patient to be treated using the combination according to the present invention, whereby the cells taken are usually taken from the tumor to be treated and the cells are manipulated so as to be genetically manipulated cells as defined herein. Subsequently, this kind of cell is administered to the patient again as part of the combination according to the present invention.

In order to increase the efficacy of the genetically manipulated cells, these cells can further express another immunomolecule. As used herein, immunomolecule comprises any molecule which is suitable to affect the immune system. Immunomolecules comprise, among others, cytokines, adhesion molecules, co-stimulatory factor, tumor-associated antigen, tumor specific antigen and parasite antigen.

In a further embodiment, the genetically manipulated cell is an allogeneic cell. An allogeneic cell is in a preferred embodiment a cell which stems from the same species, however, does not stem from the very same individual. Allogeneic cells are cells derived from the same species, but antigenically distinct. In a particularly preferred embodiment, the allogeneic cell is matched to the respective cell population of the tumor to be treated. More preferably, the match will be related to some or all human lymphocytic antigen (HLA) classes with the patients to be treated using the combination according to the present invention. However, different degrees of matching may be used. More particularly, the matching will be a HLA class I matching. HLA class I comprises sub-classes A, B and C. A HLA class I match will be given if there is a match between the cell used as the second constituent of the composition according to the present invention and the cells constituting the tumor in a patient to be treated using said composition.

It will be acknowledged that the matching and the extent of such matching required is within the skills of the ordinary person of the art. One possible experimental approach is to inoculate different groups of animals/patients with different degrees of matching and then challenge with the tumor to examine the effects. Alternatively, the test may be done to tumor patients directly.

A particularly preferred cell line is LNCaP which co-expresses interleukin-2 and interferon-gamma and which is to be used as the second constituent in connection with the combination according to the present invention, more particularly for the treatment of prostate cancer, whereby the first constituent is rBCG:Hly or rBCGΔureC:Hly.

In a further embodiment, the biologically active agent is a parasite antigen, more particularly the gp190/MSP1 protein of *Plasmodium*. Preferably, the respective antigen is derived from *Plasmodium falciparum*. Preferably, the respective antigen is derived from the amino acid sequence of the *Plasmodium* MSP-1 protein, preferably from the *Plasmodium falciparum* MSP-1 protein. The term parasite antigen as used herein, means the full length antigen as well as fragments thereof as long as they are suitable to elicit an immune response, more preferably a TH1 response or TH1 mediated response, preferably in a mammal, even more preferred in connection with the composition according to the present invention, whereby the first constituent is most preferably rBCG:Hly and rBCGΔureC:Hly, respectively.

This embodiment is particularly useful in the treatment of malaria.

It is within the present invention that such parasite antigen can be expressed by a bacterial cell acting as first constituent or the combination according to the present invention, or an eukaryotic cell acting as second constituent of the composition according to the present invention. It is, however, also within the present invention that the parasite antigen is expressed by the bacterial cell which comprises at least one recombinant nucleic acid molecule encoding a phagolysosomal escape peptide or polypeptide as specified for various embodiments of the present invention.

It is to be acknowledged that gp190/MSP consists of several naturally occurring domains and that such domains either alone or in combination can be a parasite antigen as preferably used herein. gp190/MSP1 has been regarded for quite a while as a potential candidate for a vaccine against malaria. However, its preparation has been regarded as extremely laborious not allowing large scale production of this antigen. In view of this, a potential malaria vaccine had not been made available. However, based on the technical teaching of international patent application WO 98/14583 this antigen of *Plasmodium* can now be made available in large quantities. It will be acknowledged that such parasite antigen is not limited to the gp190/MSP1 antigen but also comprises homologues thereof found in other *Plasmodium* species apart from *Plasmodium falciparum*, such as *P. vivax*. The technical teaching of said international patent application is incorporated herein by reference and allows the one skilled in the art to prepare any amount of this antigen needed so as to incorporate it into the composition according to the present invention as second constituent. DNA vaccines are, for example, described in Grode L, Mollenkopf H J, Mattow J, Stein M, Mann P, Knapp B, Ulmer J, Kaufmann S H. Application of mycobacterial proteomics to vaccine design: improved protection by *Mycobacterium bovis* BCG prime-Rv3407 DNA boost vaccination against tuberculosis. Infect Immun. 2004 November; 72(11): 6471-9.

In a further embodiment, the biologically active agent is a particle or group of viral particles or a multitude of viral particles which is preferably released after infection of mammalian cells by human cytomegalovirus (HCMV), whereby the particles (a) are surrounded by a lipid membrane in which viral glycoproteins are embedded, and (b) contain neither viral DNA nor capsids, or are dense bodies, preferably dense bodies of human cytomegalovirus. Such particles as will be described in more detail herein, are preferably used for the prevention and/or treatment of an infection by human cytomegalovirus which is a beta-herpes virus. A particularly relevant group of subjects which may be treated using the combination according to this aspect of the present invention are patients who have to undergo a bone marrow transplantation.

In immunocompetent person, HCMV infection is normally unnoticed, having at the most mild and non-specific symptoms. By contrast, in certain risk groups, for example in immunosuppressed patients such as AIDS patients or transplant recipients, and after prenatal infection, HCMV infection has serious manifestations which, therefore, constitute a further group of patients which may be treated using the combination of the adjuvant and the respective particles.

In accordance with the technical teaching of international patent application PCT/EP 00/01794 so-called dense bodies of HCMV have been proven to be efficient in terms of inducing an immune response and ultimately an immune protection against HCMV infection. Insofar, said dense bodies provide for a long lasting induction of neutralizing antibodies which protect from HCMV infection in a strain overlapping manner. This is provided by efficient induction of the so-called "helper cell response" (CD4-positive T lymphocytes) against HCMV to assist the maturation of antibody-secreting B-lymphocytes. Additionally, said dense bodies are suitable to induce the formation of cytotoxic T-cells against HCMV, whereby lymphocytes of this type are of crucial importance for terminating an HCMV infection which has taken place and limits the spread of the virus in the body. Finally, such dense bodies are suitable to minimize the side effects of a vaccine.

Dense bodies are induced by HCMV infection and released into the culture medium of infected primary human fibroblast cultures. They are structures which are visible under the electron microscope and more than 90% of whose protein mass consists of pp65. They are comparable with virus particles in being provided with a cellular lipid membrane modified by viral glycoproteins and being ejected from the cell. The viral glycoproteins are very probably in the natural confirmation in this envelope. Since dense bodies contain no viral DNA and no viral capsid, they are non-infectious. They can be concentrated in large quantity from the cell culture supernatant by established methods. Both, preventive as well as therapeutic vaccine applications can be realized using such dense bodies, particularly in combination with the adjuvant described herein.

Dense bodies are surrounded by a lipid membrane which makes it possible to fuse the particles to certain mammalian cells so that their contents enter the cytoplasm of the cell. The membrane of the particles contains viral glycoproteins which represent the main antigens for virus-neutralizing antibodies. The particles are also characterized in that they contain no viral DNA and no capsid. In addition, they contain the viral T-cell antigen pp65 (ppUL83) which both stimulates the formation of T-helper cells and is an essential antigen for inducing cytotoxic Tlymphocytes (CTL) against HCMV.

These properties, especially the combination of antigens able to induce both neutralizing antibodies and an adequate cellular response, make the particles suitable as vaccines against HCMV.

Also, dense bodies induce, irrespective of the route of administration, T-helper cell responses of the Th1 type which qualifies them as a vaccine against HCMV.

In a further embodiment, dense bodies or respective particles which contain a fusion protein which comprises in one part one or more sections of the viral T-cell antigen pp65 (ppUL83) or the protein and in another part one or more sections of one or more other proteins are described.

This makes it possible to optimize the antigenicity of the particles because this fusion protein is present in large quantity in the particles. It is additionally known that expression of antigens of the cellular and humoral immune response in one molecule can distinctly increase the antigenicity. The various sections of pp65 and the other proteins can be fused together directly but it is also possible for example to four linker sequences which are not a natural constituent of one of the proteins involved, to be present between the various sections. The sequences of this type may arise because of the cloning or be incorporated deliberately in order to influence the properties of the antigen. However, the fusion protein preferably contains no foreign sequences which are not a constituent of one of the fusion partners. In such embodiments, the fusion protein consists of one or more parts of pp65 and one or more parts of one or more other proteins.

It applies to all the embodiments mentioned hereinafter that the complete pp65 or one or more parts thereof can be present in the fusion protein. The statement "a fusion protein (consisting) of pp65" is not for the purpose of this application to be understood as restricted to complete pp65. A "part" or "section" of a protein present in the fusion protein comprises at least 6, preferably at least 8, most preferably at least 9, 15 or 20 consecutive amino acids of the protein from which it is derived.

A preferred embodiment comprises a fusion protein of pp65 (ppUL83) and one or more neutralizing epitopes of the viral glycoproteins gB or gH. Particles of this type can be generated as described in international patent application PCT/EP 00/01794. The fusion protein can enter, via antigen-specific uptake, glycoprotein-specific B cells which in turn are able to present epitopes both of the glycoproteins and of pp65 in the context of MHC class II. In addition, it is also possible for portions of the fusion protein to be presented by professional antigen-presenting cells (APC) in the context of MHC class II. In both cases the result is efficient stimulation of the $T_H$ response both to the pp65 and to viral glycoproteins. These $T_H$ cells are able to stimulate glycoprotein-specific B-cells, which present peptides of pp65 and viral glycoproteins in the context of MHC class II, to form neutralizing antibodies both homologously and heterologously. In addition, particles of this type can, like infectious virions, be taken up into cells and peptides of pp65 can be introduced by exogenous loading into the MHC class I pathway. This achieves, unusually for dead vaccines, a stimulation of the CTL response to HCMV.

In a further preferred embodiment, the particles contain a fusion protein consisting of pp65 and one or more parts of another protein of HCMV, the IE1 protein (ppUL123). The parts of the IE1 protein which are to be present in particular are those against which cytotoxic T-cells are formed in humans during natural infection. Peptides of the IE1 protein are in some cases presented by different MHC class 1 molecules than are peptides of pp65. The addition of such further "CTL" epitopes from IE1 is intended to ensure that, after immunization, inoculated subjects who express different MHC class 1 molecules are able to generate CTL against HCMV in as comprehensive a manner as possible.

In a further preferred embodiment, the particles contain a fusion protein consisting of pp65, of one or more neutralizing epitopes of HCMV glycoproteins and of one or more CTL epitopes of IE1. Fusion of pp65 with neutralizing epitopes and CTL epitopes is intended to ensure that it is possible simultaneously for both neutralizing antibodies and CTL to be formed by inoculated subjects in as comprehensive a manner as possible, i.e. by the maximum number of people differing in MHC class I pattern.

In a further preferred embodiment, the particles contain a fusion protein of pp65 and one or more epitopes of another human pathogen. Suitable portions of other human pathogens are antigens against which neutralizing antibodies are formed in humans. It is possible through a fusion of such "neutralizing antigens" with the T-cell antigen pp65 to expect a marked increase in the immune response (antibody response) compared with the use of the isolated "neutralizing an antigen". Examples of such "neutralizing antigens" which should be mentioned are surface proteins of hepatitis B virus (from the HBsAG region) of hepatitis C virus (for example E2), of human immunodeficiency viruses (HIV, from the Env region), of influenza virus (hemagglutinin, neuraminidase, nucleo-protein) or other viral pathogens. Further suitable human pathogens are bacteria such as *Haemophilus influenzae, Bordetella pertussis, Mycobacterium tuberculosis, Neisseria*, meningitidis and others. Finally, antigens from eukaryotic pathogens such as plasmodia (malaria) could be fused to pp65.

In a further preferred embodiment, the particles contain a fusion protein consisting of pp65 and one or more portions of proteins of other pathogens against which CTL are generated in humans on natural infection which these pathogens. Examples of such CTL epitopes which may be mentioned are portions of proteins of HIV-1, of HBV, of HCV or of influenza virus. The intention of such a procedure is to utilize the unique immunogenic properties of dense bodies for generating protective CTL against heterologous pathogens in humans.

In a further preferred embodiment, the particles contain a fusion protein consisting of pp65, of one or more neutralizing epitopes of a heterologous pathogen and of one or more CTL epitopes of the same pathogen. This fusion is intended to ensure that inoculated subjects are able to form both protective antibodies and CTL against this pathogen.

The invention additionally relates to viral particles containing at least two different glycoproteins which are variants of the same glycoprotein from different HCMV strains.

A preferred embodiment contains exactly two variants, one variant corresponding to the HCMV Towne strain, and the other variant corresponding to the HCMV Ad169 strain. The preferred embodiment contains the glycoprotein gB both of the Towne strain and of the Ad169 strain.

These two proteins can be incorporated with identical efficiency into the membrane of recombinant dense bodies in the infected cell. Such recombinant dense bodies are suitable for inducing not only the strain-overlapping but also the strain-specific neutralizing immune response to the two prototype HCMV strains.

Finally, the invention further relates to a method by which viral particles which are completely free of infectious virus are prepared. As preferably used herein the term free of infectious virus means that the preparations thus obtained are non-infectious with respect to the detection level. If particles are produced from a cell population which has been infected with HCMV, there is a risk that infectious virus particles will be carried along during the purification of the particles. This represents a disadvantage for a vaccine.

The method of the invention minimizes this risk. To this end, initially an HCMV strain harbouring a deletion in an essential gene is produced. By this is meant a deletion of the function of the gene. In most cases, this is based on the absence of a functional gene product, but is also possible for the function of a regulatory gene sequence to be deranged in such a way that the HCMV is no longer viable. This can take place by altering the nucleic acid sequence of HCMV, for example by point mutations, actual deletions, insertions or other mutations. This defective virus can replicate only in cells which express the gene which has been deleted in HCMV and thus make it available for assembly of the virions. Primary fibroblasts at present represent the only reasonably permissive system for the in vitro replication of HCMV. Stable transfection of such cells has to date been possible only with the aid of retroviral transfer methods. This is, however, a serious disadvantage if such cells are to be used to produce vaccines. The method of the invention makes available stably transfected cells which can be produced without retroviral gene transfer but in which HCMV can also be replicated.

A preferred embodiment comprises human foreskin fibroblasts which have been stably transfected with the major capsid protein gene UL86. The transfection is preferably carried out with a lipid-containing aid which leads to a very high transfection efficiency. In a preferred embodiment, the "Fugene reagent" which can be purchased from Roche Diagnostics, Mannheim, is employed for the transfection.

Defective virus whose major capsid protein gene UL86 has been deleted, can be replicated in these cells. If "non-complementing" fibroblasts are infected with this defective virus, it is then possible to isolate therefrom viral vaccine particles free of infectious virus particles.

Another possibility for producing the particles of the invention without the risk of infection is to reconstitute the particles in cells without infecting with HCMV. To this end, all the genes which code for constituents of the particles must be expressed in these cells. These genes must for this purpose be inserted into the cells.

Insect cells infected by baculoviruses are preferably used for this purpose. The genes which code for the polypeptide constituents of the particles are cloned into baculovirus expression vectors. The production of recombinant baculoviruses is followed by co-infection of insect cells, preferably Sf9 cells, by the various viruses. The genes are expressed in the insect cells, and the resulting polypeptides combined to give the desired particles. Finally, the particles are released by the insect cells. This represents one possibility for producing non-infectious particles which can be used as vaccines.

An alternative possibility is to clone the constituents necessary for reconstitution of dense bodies into recombinant baculoviruses under the control of the HCMV major IE promoter/enhancer (MIEP). It is shown that recombinant baculoviruses are able to infect higher eucaryotic cells such as, for example, mammalian cells, and that foreign genes under the control of a strong eucaryotic promoter such as MIEP are strongly expressed in such cells. The advantage of such a procedure would be that any important modifications, such as glycosylation, of antigenic proteins of the dense bodies could take place in a more natural manner in mammalian cells than in insect cells. In addition, there is a number of such cell lines which are already approved for vaccine production.

In a further embodiment, the biologically active agent is an antigen presenting cell, whereby such antigen presenting cell presents antigens suitable to elicit an immune response against tuberculosis and more specifically against *Mycobacterium tuberculosis, M. bovis, M. canettii, M. africanum* and *M. paratuberculosis*. In a preferred embodiment the antigen presenting cell is a microorganism, more preferably a microorganism selected from the group comprising *M. tuberculosis, M. bovis, M. canettii, M. africanum* and *M. paratuberculosis*. The combination in accordance with the present invention comprising the a bacterial cell as a first constituent and such antigen presenting cell or such antigen itself as the second constituent or as a biologically active agent, can preferably be used for the prevention and/or treatment of tuberculosis. Preferably, the antigen is antigen 85.

It is within the present invention that the first constituent of the composition according to the present invention in its various forms disclosed herein and in particular the microorganisms having a phagolysosomal escape domain in their various embodiments such rBCG:Hly and rBCG ΔureC:Hly, is acting and can thus be used as an adjuvant, which means that it is responsible for increasing the immune status of a patient to be treated or to be in need of a treatment, more preferably the immune status is related to TH1 and even more preferred the immune status is characterized by an increase in TH1 response, whereby such TH1 response is increased compared to a non-treated individual.

As disclosed herein, the second constituent is preferably physically different or physically separated from the first constituent insofar as it is to be the agent which provides for a specific biological, biochemical, physiological or medical response of the patient. The fact that the first and the second constituent are physically separated allows for an independent or separate administration of said two constituents. In case the biologically active agent is a genetically manipulated cell which expresses a cytokine and more preferably such cell being a cancer cell, the specific immune response is directed to the antigens introduced by such genetically manipulated cell. Nevertheless it has to be acknowledged that the cytokines due to their mode of action provide an overall beneficial effect which could be regarded as an adjuvant effect, too, as already provided by the first constituent.

In a further aspect the present invention is related to a pharmaceutical composition comprising the combination according to the present invention and, optionally, a pharmaceutically acceptable carrier, diluent or adjuvants or other vehicle(s). Preferably, such carrier, diluents, adjuvants and vehicles are inert, and non-toxic. The pharmaceutical composition is in its various embodiments adapted for administration in various ways. Such administration comprises systemic and local administration as well as oral, subcutaneous, parenteral, intravenous, intraarterial, intramuscular, intraperitonial, intranasal, intrategral and intraocular. A preferred pharmaceutical composition is an aqueous or physiological buffer containing both the first and the second constituent.

It will be acknowledged by the ones skilled in the art that the amount of the pharmaceutical composition to be administered depends on the clinical condition of the individual patient, the site and method of administration, scheduling of administration, patient age, sex, bodyweight and other factors known to medical practitioners. The pharmaceutically effective amount for purposes of prevention and/or treatment is thus determined by such considerations as are known in the medical arts. Preferably, the amount is effective to achieve improvement including but not limited to improve the diseased condition or to provide for a more rapid recovery, improvement or elimination of symptoms and other indicators as are selected as appropriate measures by those skilled in the medical arts.

In a preferred embodiment, the pharmaceutical composition according to the present invention may comprise other pharmaceutically active compounds.

The pharmaceutical composition is preferably formulated so as to provide for a single dosage administration or a multi-dosage administration.

In an embodiment, the first constituent and the second constituent either as such or as part of a pharmaceutical composition or as a pharmaceutical composition, are provided simultaneously, either as a single formulation or as separate formulation each. In case of a separate formulation, the first formulation contains the first constituent and the second formulation contains the second constituent. Said first and said second formulation, respectively, are in preferred embodiments formulated as any of the pharmaceutical formulations described herein.

It is also within the present invention that the first and second constituent, respectively, are separately administered. Preferably, the time difference between the first and the second constituent, respectively, is about one hour or less than one hour, preferably about 30 minutes or less, and more preferably about 15 minutes or less.

It will be acknowledged that it is also within the present invention that either the first or the second constituent or both constituents may, in the various forms as described herein, be used for the prevention of any of the diseases described herein.

FIGURE LEGENDS

The present invention will be further illustrated by reference to the figures and examples from which further features, embodiments and advantages of the invention may be taken, whereby FIG. 1 shows a diagram depicting the immune response expressed as CD8+Tet+T cells upon combined administration of BKG and vaccine compared to controls;

Figure 8:
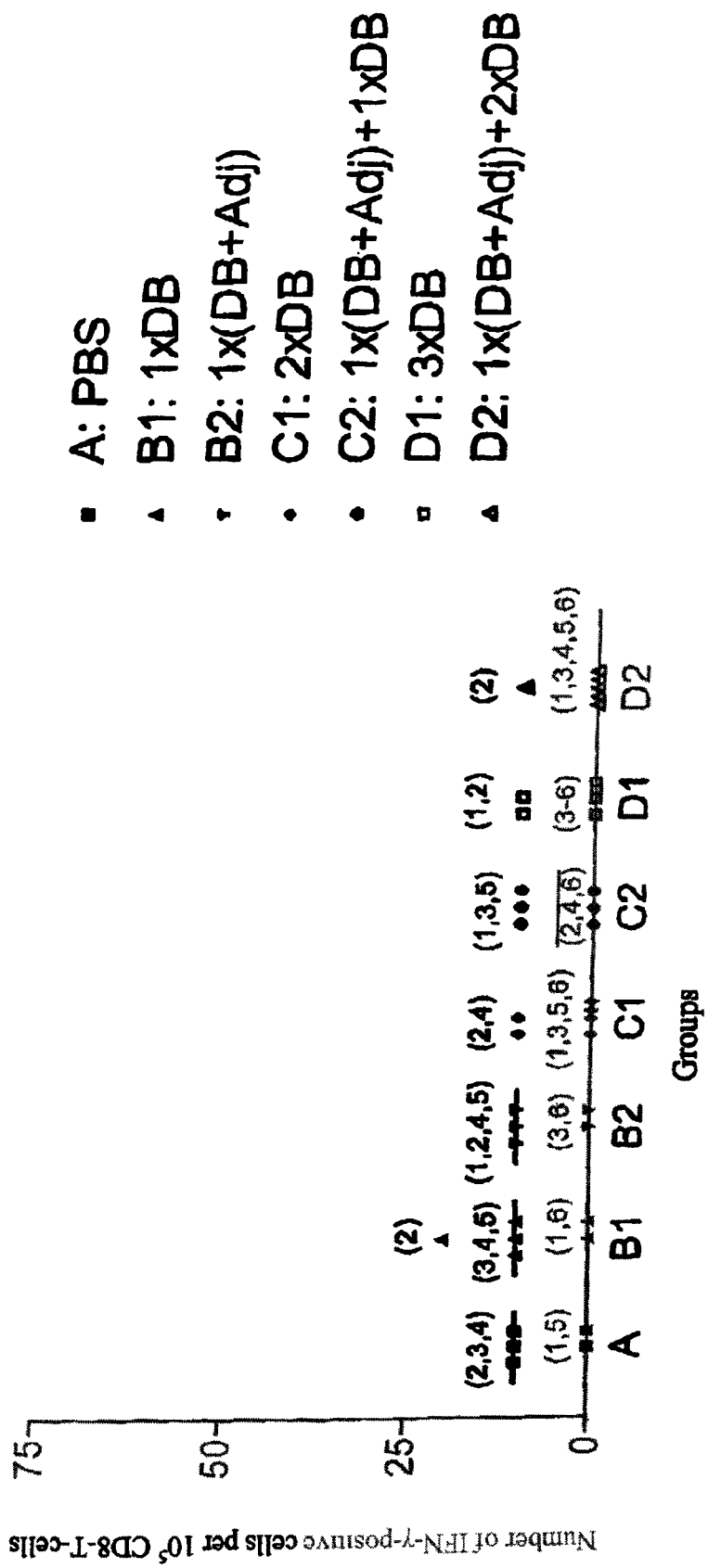
Figure 9:
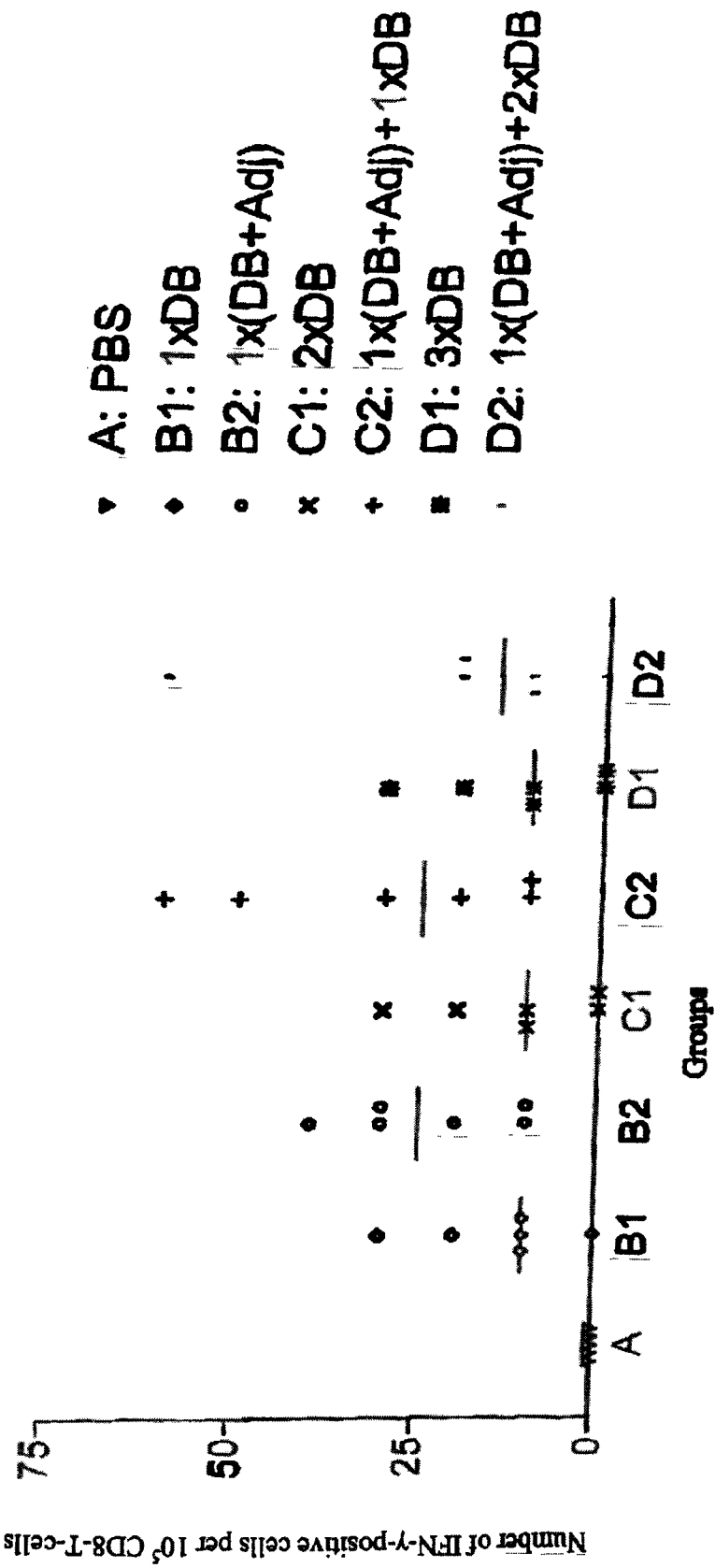

FIG. 8 is a diagram depicting the effect of different immunisation schemes on the number of IFN-gamma positive CD8 T cells upon stimulation with an unspecific control peptide; and FIG. 9 is a diagram depicting the effect of different immunisation schemes on the number of IFN-gamma positive CD8 T cells upon stimulation with an HCMV-specific peptide mix (from JPT Peptide Technologies GmbH, Berlin, Germany).

EXAMPLES

Example 1

Use of BKG as Adjuvant to a Tumor Vaccine

In this example experiments are described to determine the suitability of BKG as adjuvant to a tumor vaccine. BKG, as referred to herein, expresses the phagolysosomal escape peptide from *Listeria monocytogenes* (Hly) and is additionally ureC deficient. Such modified BCG is also referred to herein as rBCG:delta ureC:Hly.

Basically, the patients and animal models, respectively, have to be vaccinated by a standard vaccination protocol which is also referred to as prime boost-protocol. Subsequently, animals are put under a tumor challenge. Under such conditions, animals with BKG/tumor cell vaccination after tumor challenge will develop no tumor or can withstand the tumor challenge longer than the animal which got the tumor vaccination without BKG as an adjuvant. Patients with BKG/tumor cell vaccination can withstand their tumor longer compared to patients that received tumor vaccination without BKG as an adjuvant.

If not indicated to the contrary, the following materials and methods were used

Cells:

The following cell lines were used: $J558^{mOVA}$ (J558-cells expressing OVA and having bound it to the cell membrane), $J558^{sOVA}$ (J558-cells expressing OVA and secreting it into the environment) and $EL-4^{OVA}$ (EL-4-cells expressing OVA). Cell cultures were initially kept under G418-pressure for 14 days. A *Mycoplasma*-test was negative. After initial passages to increase the cell number the three cell lines were frozen in portions of $10\times10^6$ with DMSO and stored in liquid $N_2$ for at least 7 days prior to the first use within an animal.

Bacteria:

Bacteria used are labeled: BKG (rBCG delta ureC:Hly); further stated as "BKG". BKG had been grown in 7H9 complete Medium, and frozen in 10% glycerol/PBS. The bacteria could be thawed and refrozen once (but refrozen only without prior dilution).

For the primary vaccination and the following 2 boost-vaccinations 19.3 µl=1×10⁶ BKG were injected into the mice.

Vaccine Preparation:

Frozen cells were thawed and washed twice in sterile DMEM media. Subsequently cells were resuspended in sterile DMEM and counted. The total injection volume was 100 µl (prepared according to Table 1). Prior to injection cells were irradiated in a sterile syringe (150 Gy gamma radiation). In vitro controls: From thawed cells before irradiation and after irradiation, respectively, one aliquot per cell line was removed and put into cell culture. These controls showed good recovery after thawing (non-irradiated cells) and no cell proliferation for more than 14 days after the irradiation.

Mice:

C57/B6 female 12 weeks old (delivered at the age of 6 weeks and accommodated to the test laboratory for 6 weeks); vaccinated s.c. 100 µl; 25 G needle; base of the tail; after 7 days 0.3 ml of blood for immunomonitoring (tetramer for OVA) removed under general anaesthesia. The usage of the mice was accepted by the respective authorities.

Schedule of the BKG exp. #1:

| day 0 | Primary Vaccination (Prime) |
|---|---|
| 7 days | 1$^{st}$ blood collection |
| 28 days | 1$^{st}$ booster vaccination (1$^{st}$ Boost) |
| 35 days | 2$^{nd}$ blood collection |
| 53 days | 2$^{nd}$ booster vaccination (2$^{nd}$ Boost) |
| 60 days | 3$^{rd}$ blood collection |
| 74 days | Tumor challenge |

The used mice are divided into 2 experimental and one control groups:
Vaccine group plus BKG (n=9): subgroups #1.1, #1.3 and #1.5 (see table 1)
Vaccine group minus BKG (n=9): subgroups #1.2, #1.4 and #1.6
Control-group (n=2): subgroup #1.7

TABLE 1

| | | | | | | | | |
|---|---|---|---|---|---|---|---|---|
| Exp. Group | Cells | BKG | DMEM [µl] | BKG [n] | BKG [µl] | Cells [n] | Cells [µl] | n = |
| #1.1 | J558$^{mOVA}$ | + | — | 1 × 10⁶ | 19.3 | 10 × 10⁶ | 80.7 | 3 |
| #1.2 | J558$^{mOVA}$ | − | — | — | — | 10 × 10⁶ | 100.0 | 3 |
| #1.3 | J558$^{sOVA}$ | + | — | 1 × 10⁶ | 19.3 | 10 × 10⁶ | 80.7 | 3 |
| #1.4 | J558$^{sOVA}$ | − | — | — | — | 10 × 10⁶ | 100.0 | 3 |
| #1.5 | EL-4$^{OVA}$ | + | — | 1 × 10⁶ | 19.3 | 10 × 10⁶ | 80.7 | 3 |
| #1.6 | EL-4$^{OVA}$ | − | — | — | — | 10 × 10⁶ | 100.0 | 3 |
| #1.7 | Ctr | − | 100 | — | — | — | — | 2 |
| | | | | | | | | 20 |

Housing of the Animals:

S2-conditions, IVC-cages, 2 cages; change interval 3-4 days.

FACS Analysis:

A FACS-run was performed to detect the amount of SIINFEKEL (SEQ ID NO:3)-specific T cells in a blinded manner. After sorting the cellular components the plasma is frozen and stored for further evaluation at −80° C.

Parallel In Vitro-Experiments:

| Cell culture | generating the cells for vaccination and tumor challenge<br>In vitro-Controls of the cells used within the animal experiments<br>Cell cultures of the cells used as controls in the FACS experiments, producing the tetramers |
|---|---|
| Vectorology | A vector (SINvector) has been designed recombinant for IL-2, IFNgamma and OVA. This vector is used to create a mouse tumor cell line corresponding to the LNCaP-IL-2-IFNgamma cells. |

Figure 1:
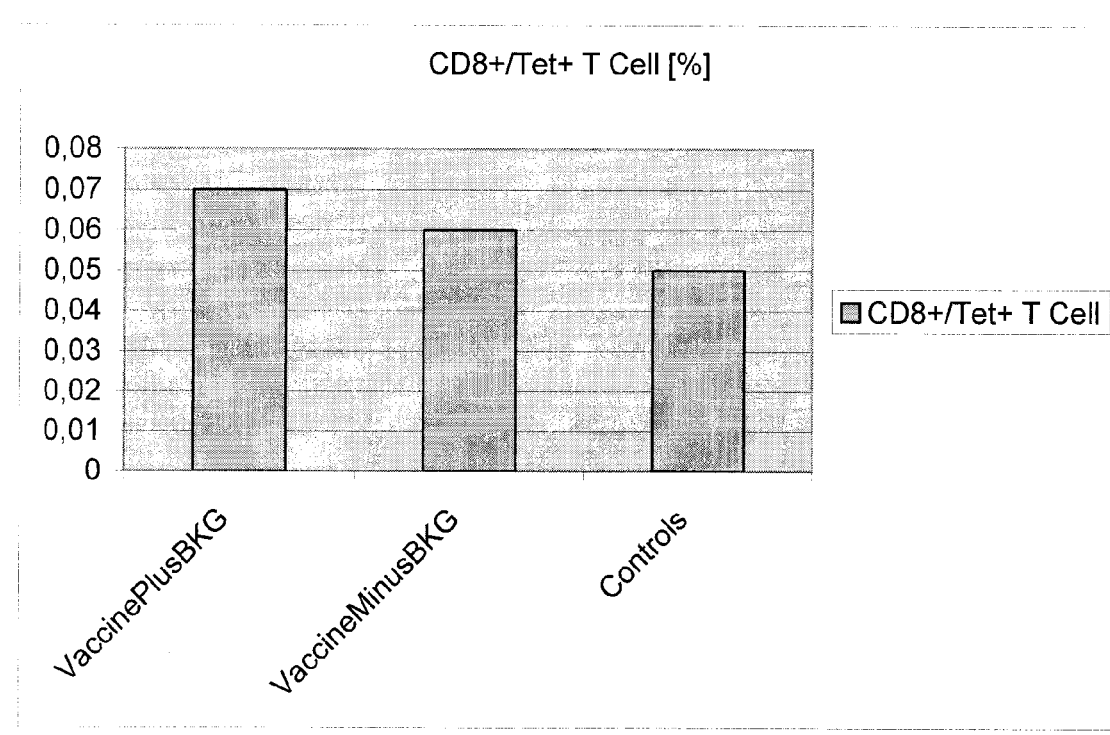

Results:

The first results of the immunological monitoring as depicted in FIG. 1 show that there is a trend to a higher amount of T-cells being able to recognize the OVA-peptide in the group of mice having BKG as an adjuvant than in the group of animals which had no adjuvant. This supports that BKG is an adjuvant to a tumor vaccination which enhances the immunological response to the vaccine.

Example 2

Optimization of the Treatment Regimen for Tumor Vaccination Using BKG

The following is a protocol for optimizing the administration regimen of the therapeutic concept outlined in Example 1 so as to allow the one skilled in the art to optimize the basic treatment regimen disclosed herein. The materials and methods are as outlined in connection with the Example 1 above, if not indicated to the contrary.

Regimen 1:

Using the stably triple-transfected J558 (H2 K$^b$) cell line expressing IL-2, IFNgamma and ovalbumin, three different doses of these cells are injected into mice (C57 BL/6 (H2 K$^b$)), namely 5×10⁶-cells, 10×10⁶-cells and 15×10⁶-cells. For each dosage the group of mice consists of five animals and their injection scheme is as follows: prime immunization with three boosts every 30 days; whereby the injection occurs with or without BKG (1×10⁶ CFU). The animals are immunologically examined whether or not they show ovalbumin-specific immune response, and in particular an increase in the immune response mediated by BKG.

Regimen 2:

This trial consists of a series of Preliminary Experiments ("Preliminary Experiments 1 to 7") and four major experiments ("Experiments 1 to 4").

Preliminary Experiment 1

Dosage Finding of the Vaccination Tumor with and without BKG as Adjuvant

A total of 14 groups of mice each consisting of five mice (C57 BL/6 (H2 $K^b$)) are immunized with increasing dosages of the vaccination tumor (each 2 of the 14 groups receive the same dosage of vaccination tumor). The vaccination tumor consists of irradiated ovalbumin expressing allogeneic J558 tumor cells (H2 $K^b$)) which are injected s.c. BKG at a dosage of $1\times10^6$ CFU is injected together with the tumor cells in seven groups. After one week as well as 5, 9 and 13 weeks, 0.5 ml of blood is taken from the animals and ovalbumin-specific immune reaction is tested by means of ELISA, intracellular cytokine staining or tetramer staining. A total of seven different cell dosages of the vaccination tumors with or without BKG is used. The respective dosages are $0.11\times10^6$, $0.5\times10^6$, $1.0\times10^6$, $5.0\times10^6$, $10.0\times10^6$, $50.0\times10^6$, $100\times10^6$ whereby corresponding clinical trials in human beings use dosages with a preferred range of $10\times10^6$ to $300\times10^6$ cells. Mice in the total of 2 control groups receive no vaccination tumor. One control group receives a BKG injection.

Preliminary Experiment 2

Dosage Finding of Test Tumor B16$_{OVA}$ Melanoma)

In this trial, four groups of mice (C57 BL/6(H2$K^b$)) receive increasing dosages of the test tumor (B16$_{OVA}$ melanoma s.c.). Tumor growth is monitored until the tumor volume reaches 2 cm. Once this tumor volume is reached, the mice are euthanized, the blood and tumor material recovered and stored for in vitro analysis. If there is no tumor growth, the mice are sacrificed after 12 weeks. Again, each group consists of five mice, whereby four different cell dosages of the test tumor are used, namely $1.0\times10^6$ cells, $5.0\times10^6$, $10.0\times10^6$ and $50.0\times10^6$ cells.

Preliminary Experiment 3

Determination of Adjuvant Dosage

Based on the dosage identified in Preliminary Experiment 1, the dosage of BKG is varied, whereby the dosage of the adjuvant is varied by a factor of 10, 100 and 1000 and 0.1, 0.01 and 0.001 compared to the dosage which is used in the Preliminary Experiment 1. After one week as well as 5, 9 and 13 weeks, 0.5 ml of blood is taken from the animals and ovalbumin-specific immune reaction is tested by means of ELISA, intracellular cytokine staining or tetramer staining.

Preliminary Experiment 4

Studies on the Administration Mode

The dosage of the vaccination tumor cells determined in Preliminary Experiment 1 and the dosage of BKG determined in Preliminary Experiment 3 is varied with regard to the mode of administration. Modes of administration are intravenous, intradermal, intraperitoneal and ipsilaterally s.c. For each administration mode the dosage of BKG is either one times, 0.1 times or 0.01 times the dosage as defined in Preliminary Experiment 3. The modes of administration tested herein are similar to a potential clinical use with humans and differ with regard to the compartment of the immune system which has first contact with the adjuvant. After one week as well as 5, 9 and 13 weeks, 0.5 ml of blood is taken from the animals and ovalbumin-specific immune reaction is tested by means of ELISA, intracellular cytokine staining or tetramer staining.

Preliminary Experiment 5

Studies on the Immunization Scheme

Using the dosage of the vaccination tumor cells as defined in Preliminary Experiment 1 and the BKG dosage determined in Preliminary Experiment 3 the following immunization schemes are examined:

| | |
|---|---|
| 1. Immunization scheme 1: | a single co-injection of vaccination tumor and adjuvants (control groups) |
| 2. Immunization scheme 2: | this scheme corresponds to the prophylactic immunization of some diseases like measles, whereby there is a triple basic immunization and a boost, whereby the basic immunization is performed at the beginning, after two and four weeks and a Boost is administered after further six weeks. |
| 3. Immunization scheme 3: | this scheme corresponds to a scheme which turned out to be essential for therapeutic vaccination going along with an ongoing application of the vaccines in a distinct vaccination interval. More specifically, the following three subschemes can be defined. |
| Immunization scheme 3a: | vaccination every 3 weeks (last blood sampling and euthanasia after 12 weeks); |
| Immunization scheme 3b: | vaccination every 6 weeks (last blood sampling and euthanasia after 25 weeks); |
| Immunization scheme 3c: | vaccination every 12 weeks (last blood sampling and euthanasia after 43 weeks). |

All three immunization schemes are repeated, whereby the dosage of the adjuvant BKG is either the dosage determined in Preliminary Experiment 3, or the 10-fold or 0.1-fold dosage thereof.

Preliminary Experiment 6

Dosage Finding of the Vaccination Tumor (TRAMP) with and without BKG

A total of 12 groups of TRAMP mice (Jackson Laboratory Lines Nos. 003135) are vaccinated with 0.1-fold, 1-fold, and 10-fold the dosage of TRAMP-C1 vaccination tumor cells defined in literature ($5 \times 10^6$ cells). The vaccination tumor cells are used either without any genetic modification (wt-TRAMP) or as IL-2/IFNgamma transfected cells. Mice are immunised s.c. using $5 \times 10^5$, $5 \times 10^6$ and $5 \times 10^7$ TRAMP cells. Six groups receive $1 \times 10^6$ CFU BKG as active adjuvant together with the tumor cells. One week after immunisation and subsequently after each six weeks 0.5 ml blood is sampled and TRAMP-C1-specific immune reaction is determined by ELISA, intracellular cytokine staining or tetramer staining. Every twelve weeks a CT is run in order to monitor the progress of the disease. TRAMP mice which experience an unaffected prostate cancer disease have to be sacrificed at the age of 32 to 35 weeks in order to avoid unnecessary suffering. In order to explore whether due to the vaccination a change in the progress of the disease can be observed, the mice shall be observed until the $40^{th}$ week.

Preliminary Experiment 7

Studies on Adjuvant Dosage

The dosage of the vaccination tumor cells determined in Preliminary Experiment 6 is varied with regard to the BKG dosage (0.1-fold, 1-fold and 10-fold the BKG dosage determined in Preliminary Experiment 6). Similar to Preliminary Experiment 6 both wtTRAMP-C1 as well as genetically engineered IL-2/IFNgamma-TRAMP-C1 cells are tested. One week after immunisation and subsequently every six weeks, samples of 0.5 ml blood are retrieved from the animals and TRAMP-C1 specific immune reaction is determined by ELISA, intracellular cytokine staining or tetramer staining. Every twelve weeks a CT is run in order to monitor the progress of the disease. The last blood sampling and euthanasia is performed at week 40.

Experiment 1

Prophylactic Tumor Vaccination Using the Ovalbumin System

C57BL/6 mice (H2 $K^b$) are immunised using vaccination tumor cells, i.e. irradiated ovalbumin-expressing allogeneic J558 tumor cells (H2 $K^b$) with a dosage as defined in Preliminary Experiment 1. Some of the animals receive the active adjuvant BKG (dosage defined in Preliminary Experiment 3) together with the vaccination tumor. After one week 0.5 ml blood is retrieved from the animals and ovalbumin specific immune reaction is determined by ELISA, intracellular cytokine staining or tetramer staining. After another four weeks the reactivity of the immune system against live tumor cells is determined by means of s.c. injection of ovalbumin expressing B16 tumor cells and regular control of tumor growth with the dosage of the tumor cells corresponding to the one determined in Preliminary Experiment 2.

Additionally, the effect of BKG on the increase of tumor-specific immune reaction is compared to wildtype BCG bacteria. As a mode of administration the best mode as determined in Preliminary Experiment 4 is used in combination with the two optimum immunisation schemes determined in Preliminary Experiment 5 comprising the best prime boost scheme and the best continuous application scheme.

Experiment 2

Therapeutic Tumor Vaccination Using the Ovalbumin System

In contrast to the prophylactic tumor immunisation as reported in experiment 1, a tumor growth is generated in C57BL/6 mice (H2 $K^b$) by s.c. injection of the non-irradiated test tumor cells using the dosage as identified in Preliminary Experiment 2. Once the tumor has a diameter of 0.5 cm the vaccination schemes described in Experiment 1 are tested. The tests are stopped once the tumor has reached a diameter of 2 cm. However, the animals are monitored for a maximum of one year. In order to reflect the occurring immunological processes, 0.5 ml blood is sampled from the mice every four weeks in order to determine immune response as defined in experiment 1.

Experiment 3

Prophylactic Tumor Vaccination (TRAMP)

TRAMP mice show first intraepithelial neoplasia in the sixth to seventh week and marked clinical picture of prostate carcinoma starting from the $15^{th}$ week. Such prostate carcinoma is locally limited in the beginning, but starting from week 24 on about 10% of the animals develop metastasis and severe disease conditions can be expected starting from week 32 to 35. Prophylactic tumor vaccination starts from the $5^{th}$ week on. A single injection of vaccination tumor cells without adjuvant and with adjuvants is used. As vaccination tumor cells lethally radiated TRAMP-C1 cells are used which is a prostate carcinoma cell line derived from TRAMP mice. The vaccination tumor cells are used either without being genetically engineered (wtTRAMP) or as IL-2/IFNgamma-transfected cells. Additionally the two best immunisation schemes (prime boost scheme and long-term scheme) as determined in the Preliminary Experiments are tested. As control of the PCa development the animals shall be subjected to CT every twelve weeks. The following groups can be defined:

| | | |
|---|---|---|
| HV3.1 | without vaccination (control group) | |
| HV3.2 | vaccination tumor only (wtTRAMP-C1 cells) s.c. | |
| HV3.3 | BKG vaccine (wtTRAMP-C1 cells + BKG) s.c. | |
| HV3.4 | BCG vaccine (wtTRAMP-C1 cells + BCG) s.c. | |
| HV3.5 | vaccination tumor only (wtTRAMP) as prime boost as determined in Preliminary Experiment 5 | |
| HV3.6 | BKG vaccine (wtTRAMP) as prime boost as determined in Preliminary Experiment 5 | |
| HV3.7 | BCG vaccine (wtTRAMP) as prime boost as determined in Preliminary Experiment 5 | |
| HV3.8 | vaccination tumor only (wtTRAMP) as long-term immunisation as determined in Preliminary Experiment 5 | |

| | |
|---|---|
| HV3.9 | BKG vaccine (wtTRAMP) as long-term immunisation as determined in Preliminary Experiment 5 |
| HV3.10 | BCG vaccine (wtTRAMP) as long-term immunisation as determined in Preliminary Experiment 5 |
| HV3.11 | vaccination tumor only (IL2/IFNgamma-TRAMP-C1 cells) s.c. |
| HV3.12 | BKG vaccine (IL2/IFNgamma-TRAMP-C1 cells + BKG) s.c. |
| HV3.13 | BCG vaccine (IL2/IFNgamma-TRAMP-C1 cells + BCG) s.c. |
| HV3.14 | vaccination tumor only (IL2/IFNgamma-TRAMP) as prime boost as determined in Preliminary Experiment 5 |
| HV3.15 | BKG vaccine (IL2/IFNgamma-TRAMP) as prime boost as determined in Preliminary Experiment 5 |
| HV3.16 | BCG vaccine (IL2/IFNgamma-TRAMP) as prime boost as determined in Preliminary Experiment 5 |
| HV3.17 | vaccination tumor only (IL2/IFNgamma-TRAMP) as long-term immunisation as determined in Preliminary Experiment 5 |
| HV3.18 | BKG vaccine (IL2/IFNgamma-TRAMP) as long-term immunisation as determined in Preliminary Experiment 5 |
| HV3.19 | BCG vaccine (IL2/IFNgamma-TRAMP) as long-term immunisation as determined in Preliminary Experiment 5 |

Figure 2:
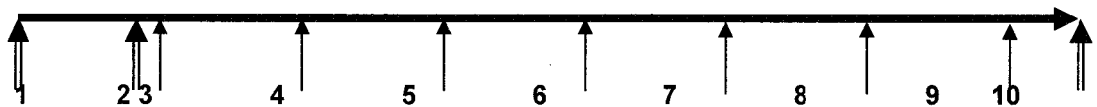
FIG. 2 shows immunisation schemes for prophylactic tumor vaccination of groups HV3.2 to HV3.4 and HV3.11 to HV3.13.
Figure 3:
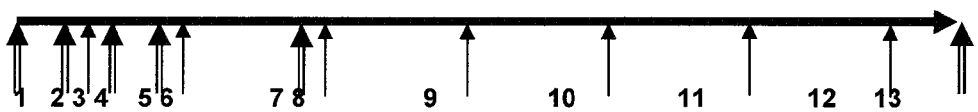
FIG. 3 shows immunisation schemes for prophylactic tumor vaccination of groups HV3.5 to HV3.7 and HV3.14 to HV3.16.
Figure 4:
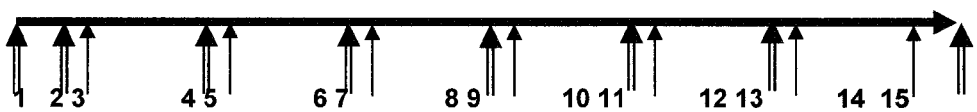
FIG. 4 shows immunisation schemes for prophylactic tumor vaccination of groups HV3.8 to HV3.10 and HV3.17 to HV3.19.

The immunisation scheme of groups HV3.2 to HV3.4 and HV3.11 to HV3.13 is depicted as FIG. 2 with the numerals representing
1: birth of mice; week −5
2: vaccination; time 0 (mice at the age of 5 weeks)
3: blood sampling after one week
4: blood sampling after seven weeks
5: blood sampling and CT after 13 weeks
6: blood sampling after 19 weeks
7: blood sampling and CT after 25 weeks
8: blood sampling after 31 weeks
9: blood sampling and CT after 37 weeks
10: blood sampling after 40 weeks and euthanasia of the mice
The immunisation scheme of groups HV3.5 to HV3.7 and HV3.14 to HV3.16 is depicted as FIG. 3 with the numerals representing
1: birth of mice; week −2
2: vaccination; time 0 (prime I)
3: blood sampling after one week
4: vaccination after two weeks (prime II)
5: vaccination after four weeks (prime III) (at the age of 6 weeks)
6: blood sampling after five weeks
7: vaccination after ten weeks (booster vaccination) (at the age of 12 weeks)
8: blood sampling and CT one week after booster vaccination
9: blood sampling seven weeks after booster vaccination
10: blood sampling and CT 13 weeks after booster vaccination
11: blood sampling 19 weeks after booster vaccination
12: blood sampling and CT 25 weeks after booster vaccination
13: blood sampling 28 weeks after booster vaccination (at the age of 40 weeks) and euthanasia of the mice
The immunisation scheme of groups HV3.8 to HV3.10 and HV3.17 to HV3.19 is depicted as FIG. 4 with the numerals representing
1: birth of mice; week −2
2: first vaccination; time 0
3: blood sampling after one week
4: second vaccination after six weeks (interval of vaccination as determined in Preliminary Experiment 5)
5: blood sampling after one week
6: third vaccination after twelve* weeks
7: blood sampling and CT after one week
8: fourth vaccination after 18* weeks
9: blood sampling after one week
10: fifth vaccination after 24* weeks
11: blood sampling and CT after one week
12: sixth vaccination after 30* weeks
13: blood sampling after one week
14: blood sampling after six weeks
15: blood sampling after 40 weeks and euthanasia of the mice
* interval of vaccination depends on the results from Preliminary Experiment 5

Experiment 4

Therapeutic Tumor Vaccination (TRAMP)

All TRAMP mice develop a prostate tumor at the age of 15 weeks which is fully developed at week 32 and causes clinical problems to the animals. Therefore, the animals are to be immunised at week 24. The experiment is stopped once one of the stop criteria is realised. At a maximum, the animals are to be monitored for 40 weeks. In order to monitor the immunological processes a blood sample of 0.5 ml is taken from the mice every six weeks and the immune response studied as described in connection with experiment 1, and an imaging procedure is used such as CT, every twelve weeks. The same tumor cells as described in connection with experiment 3 are used.

The following groups are tested.

| | |
|---|---|
| HV4.1 | no vaccination (control group) |
| HV4.2 | vaccination tumor only (wtTRAMP-C1 cells) s.c.) |
| HV4.3 | BKG vaccine (wtTRAMP-C1 cells + BKG) s.c. |
| HV4.4 | BCG vaccine (wtTRAMP-C1 cells + BCG) s.c. |
| HV4.5 | vaccination tumor only (wtTRAMP) as prime boost as determined in Preliminary Experiment 5 |
| HV4.6 | BKG vaccine (wtTRAMP) as prime boost as determined in Preliminary Experiment 5 |

| | |
|---|---|
| HV4.7 | BCG vaccine (wtTRAMP) as prime boost as determined in Preliminary Experiment 5 |
| HV4.8 | vaccination tumor only (wtTRAMP) as long-term immunisation as determined in Preliminary Experiment 5 |
| HV4.9 | BKG vaccine (wtTRAMP) as long-term immunisation as determined in Preliminary Experiment 5 |
| HV4.10 | BCG vaccine (wtTRAMP) as long-term immunisation as determined in Preliminary Experiment 5 |
| HV4.11 | vaccination tumor only (IL2/IFNgamma-TRAMP-C1 cells) s.c. |
| HV4.12 | BKG vaccine (IL2/IFNgamma-TRAMP-C1 cells + BKG) s.c. |
| HV4.13 | BCG vaccine (IL2/IFNgamma-TRAMP-C1 cells + BCG) s.c. |
| HV4.14 | vaccination tumor only (IL2/IFNgamma-TRAMP) as prime boost as determined in Preliminary Experiment 5 |
| HV4.15 | BKG vaccine (IL2/IFNgamma-TRAMP) as prime boost as determined in Preliminary Experiment 5 |
| HV4.16 | BCG vaccine (IL2/IFNgamma-TRAMP) as prime boost as determined in Preliminary Experiment 5 |
| HV4.17 | vaccination tumor only (IL2/IFNgamma-TRAMP) as long-term immunisation as determined in Preliminary Experiment 5 |
| HV4.18 | BKG vaccine (IL2/IFNgamma-TRAMP) as long-term immunisation as determined in Preliminary Experiment 5 |
| HV4.19 | BCG vaccine (IL2/IFNgamma-TRAMP) as long-term immunisation as determined in Preliminary Experiment 5 |

Figure 5:
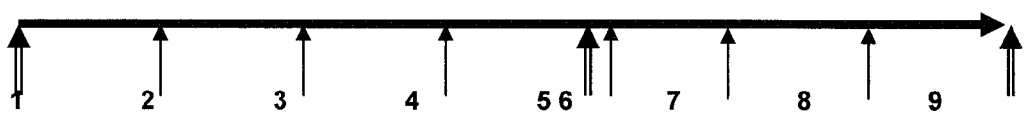
FIG. 5 shows immunisation schemes for therapeutic tumor vaccination for groups HV4.2- HV4.4 and HV4.11- HV4.13.
Figure 6:
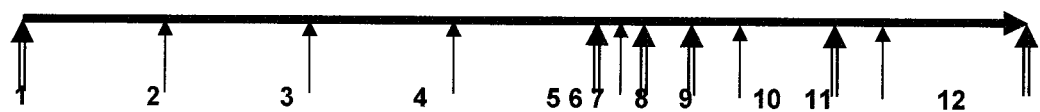
FIG. 6 shows immunisation schemes for therapeutic tumor vaccination for groups HV4.5 to HV4.7 and HV4.14 to HV4.16.
Figure 7:
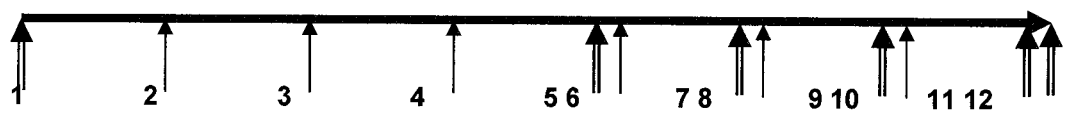
FIG. 7 shows immunisation schemes for therapeutic tumor vaccination for groups HV4.8 to HV4.10 and HV4.17 to HV4.19.

FIG. 5 shows the immunisation scheme 1 for groups HV4.2-HV4.4 and HV4.11-HV4.13 with the numerals representing 1: birth of mice
2: blood sampling after six weeks
3: blood sampling and CT after twelve weeks
4: blood sampling after 18 weeks
5: vaccination after 24 weeks
6: blood sampling and CT after 25 weeks
7: blood sampling after 30 weeks
8: blood sampling and CT after 36 weeks
9: blood sampling after 40 weeks and euthanasia of the mice FIG. 6 shows the immunisation scheme 2 for groups HV4.5 to HV4.7 and HV4.14 to HV4.16 with the numerals representing 1: birth of mice
2: blood sampling after six weeks
3: blood sampling and CT after twelve weeks
4: blood sampling after 18 weeks
5: vaccination after 24 weeks (prime I)
6: blood sampling and CT after 25 weeks
7: vaccination after 26 weeks (prime II)
8: vaccination after 28 weeks (prime III)
9: blood sampling after 30 weeks
10: vaccination (booster vaccination) after 34 weeks
11: blood sampling and CT after 36 weeks
12: blood sampling after 40 weeks and euthanasia of the mice FIG. 7 shows the immunisation scheme 3 for groups HV4.8 to HV4.10 and HV4.17 to HV4.19 with the numerals representing 1: birth of mice
2: blood sampling after six weeks
3: blood sampling and CT after twelve weeks
4: blood sampling after 18 weeks
5: vaccination after 24 weeks (prime I)
6: blood sampling and CT after 25 weeks
7: vaccination after 30 weeks (prime II)
8: blood sampling after 31 weeks
9: vaccination after 36 weeks (prime III)
10: blood sampling and CT after 37 weeks
11: vaccination after 42 weeks (prime IV)
12: blood sampling after 43 weeks and euthanasia of the mice The vaccination intervals preferably depend on results of Preliminary Experiment 5.

Example 3

Composition for the Treatment of Prostate Cancer

A composition which is suitable for the treatment of prostate cancer contains as a first constituent BCG which expresses the phagolysosomal escape peptide from *Listeria monocytogenes* (Hly) and is additionally ure C-deficient. Such modified BCG is also referred to herein as rBCG: delta ureC: Hly. The composition contains as second constituent genetically engineered LNCaP cells These cells are prostate carcinoma cells expressing recombinant interleukin-2 (IL2) and interferon-gamma (IFN gamma). Preferably, such LNCaP cells express both cytokines in an about equimolar manner. This kind of LNCaP cells are, e.g. described in international patent application WO 94/18995. Such recombinant prostate cancer cells were irradiated with gamma-rays in order to destroy their capability to replicate prior to the use.

Both constituents were suspended in a phosphate buffered saline solution and provided for administration to a patient. The composition contains $1 \times 10^6$ BCG cells and $1 \times 10^6$ LNCaP cells contained in 50 µl. The composition is injected i. v. In order to test the efficacy a ELISPOT analysis is performed. Such ELISPOT analysis is, for example, described in Mollenkopf H. J., Dietrich G., Fensterle J., Grode L., Diehl K. D., Knapp B., Singh M., O'Hagan D. T., Ulmer J. B., and Kaufmann S. H. Enhanced protective efficacy of a tuberculosis DNA vaccine by adsorption onto cationic PLG microparticles. Vaccine. 2004 Jul. 29; 22(21-22):2690-5.

In an alternative treatment regimen, the aforementioned composition is administered once, followed by further administration of the LNCaP cells only. Insofar, it is a general principle of the present invention that the first and second constituent can be administered at a different frequency and following a different time pattern.

In clinical testing histology and clinical tumor stadium as well as the health status of the patients thus treated is registered. A surrogate parameter will be the course of the PSA level and the number of patients having a favourable course of the PSA level.

Due to the particular combination administered to the patient a favourable course of both the PSA level as well as an improved survival rate will be observed which is higher compared to the effects seen without the adjuvant i.e. upon administration of the LNCaP cells only.

Example 4

Use of BKG as Adjuvant to an HCMV Vaccine

This example reports the successful combination of BKG as an adjuvant and HCMV dense bodies as described herein in order to induce cellular immunity against infection with human cytomegalovirus. More particularly, it is reported that cellular immunity can be induced within a short period of time. Such fast induction of HCMV immunity is particularly important in patients undergoing a bone marrow transplantation which goes along with a life threatening HCMV infection quite frequently. For transplantation patients there is a need for rapid generation of cellular immunity as there is no time for a vaccination over a longer period of time in accordance with standard practice.

The following vaccination scheme was used:

| Antigen: dense bodies | dosage: | 20 µg/animal |
|---|---|---|
| | immunization scheme: | D: day 0/7/21 |
| | | C: day 0/7 |
| | | B: day 0 |
| Adjuvant: | dosage: | 1 × 10$^6$/animal |
| | immunization scheme: | day 0 |

Structure of Groups:

| Gr. | Number of animals | Vaccines (per animal) day 0 | Vaccines (per animal) day 7 | Vaccines (per animal) day 21 |
|---|---|---|---|---|
| A | 4 | | | |
| B1 | 6 | 20 µg dense bodies | | |
| B2 | 6 | 20 µg dense bodies + 1 × 10$^6$ BKG | | |
| C1 | 6 | 20 µg dense bodies | 20 µg dense bodies | |
| C2 | 6 | 20 µg dense bodies + 1 × 10$^6$ BKG | 20 µg dense bodies | |
| D1 | 6 | 20 µg dense bodies | 20 µg dense bodies | 20 µg dense bodies |
| D2 | 6 | 20 µg dense bodies + 1 × 10$^6$ BKG | 20 µg dense bodies | 20 µg dense bodies |

Preparation is done each 8 and 9 days, respectively, after the last immunization.

The results are depicted in FIGS. 8 and 9, whereby FIG. 9 is a diagram depicting the number of IFN-gamma-positive cells per 10$^5$ CD8+ T cells upon stimulation with an HCMV-specific peptide mix (from JPT Peptide Technologies GmbH, Berlin, Germany). The sequences are taken from the HCMV pp65 protein. It is a mix (Pepmix) of 138 peptides (15 amino acids, each) that show sequence overlaps of 11 amino acids). FIG. 8 is a diagram similar to the one of FIG. 9, whereby the respective number of CD8+ T cells was determined upon stimulation with an unspecific control peptide. As may be taken from said figures, in case BKG was used as an adjuvant at the initial vaccination, in each cases, the number of IFN-gamma-positive CD8 cells per 10$^5$ CD8. T-cells significantly increased. The most pronounced increase can be observed in groups B2 and C2. This means that a basic vaccination with BKG in combination with dense bodies, whereby the dense bodies are administered at day 0 and after 7 days, is already sufficient to significantly increase the number of IFN-gamma-positive cells. This confirms the surprising finding underlying the present invention that it is possible to induce cellular immunity against HCMV when combining both dense bodies and BKG.

Example 5

Composition for the Treatment and Prevention of Malaria

A composition for the treatment and prevention of malaria comprises as first constituent rBCG: delta ure C: Hly and as second constituent the malaria antigen gp190/MSP1. It will be acknowledged that the antigen can be either present as a peptide or be part of a larger peptide, polypeptide or even protein.

The composition comprises 50 µg of the MSP1 protein and about 1×10$^6$ rBCG:delta ureC:Hly in 50 µl of a PBS buffer. The composition is administered s. c. in mice. After the immunisation the spleen and the blood of the immunised mice will be collected and use in analytic methods.

The progress of the vaccination process is again monitored using the ELISPOT technology (Mollenkopf H. J., supra) and a Merozoite invasion-inhibition assay (Blackman et al. 1990J. Exp. Med. Volume 172 P: 379-382). We expect an improved immune stimulation and IFN-gamma secretion after stimulation with MSP-1 specific peptides. We also expect invasion-inhibition induced by the collected sera from immunised mice. The IFN-gamma ELISPOT and Merozoite-inhibition results are correlates of protections.

The features of the present invention disclosed in the specification, the claims, the sequence listing and/or the drawings may both separately and in any combination thereof be material for realizing the invention in various forms thereof.

What is claimed is:

1. A Th1 immune response-eliciting combination comprising a first constituent, wherein the first constituent is a bacterial cell active as an adjuvant which comprises at least one recombinant nucleic acid molecule encoding a *Listeria* phagolysosomal escape peptide or a *Listeria* phagolysosomal escape polypeptide, wherein the bacterial cell is a urease-deficient *Mycobacterium* cell and a separate second constituent, wherein the second constituent is an immune response-eliciting biologically active agent selected from the group consisting of a tumor-specific antigen, a tumor-associated antigen, a virus antigen, a bacterial antigen, a parasite antigen, and a eukaryotic cell which expresses a cytokine, wherein the combination elicits the Th1 immune response in a mammal.

2. The combination of claim 1, wherein the *Mycobacterium* cell is a *Mycobacterium bovis* cell.

3. The combination of claim 1, wherein at least one cellular urease subunit-encoding nucleic acid of the *Mycobacterium* cell is inactivated.

4. The combination according to claim 3, wherein the inactivated at least one cellular urease subunit-encoding nucleic acid is the *Mycobacterium* urease C subunit-encoding sequence.

5. The combination according to claim 1, wherein the phagolysosomal escape peptide or the phagolysosomal escape polypeptide is a *Listeria monocytogenes* phagolysosomal escape domain.

6. The combination according to claim 1, wherein the phagolysosomal escape peptide or the phagolysosomal escape polypeptide is encoded by a nucleic acid molecule selected form the group consisting of:
    (a) a nucleotide sequence comprising nucleotides 211 to 1722 of SEQ ID NO: 1;
    (b) a nucleotide sequence which encodes for an amino acid sequence encoded by the nucleotide sequence from (a) and
    (c) a nucleotide sequence which hybridizes under stringent conditions with the sequence from (a) or (b), wherein said stringent conditions corresponding to conditions in which a positive hybridization signal is observed after washing for one hour with at least 1×SSC and 0.1% SDS at a temperature of 55° C., 62° C., or 68° C.

7. The combination according to claim 1, wherein the *Mycobacterium* cell is rBCG:Hly or rBCGΔureC:Hly.

8. The combination according to claim 1, wherein the biologically active agent is a eukaryotic cell or a genetically manipulated eukaryotic cell which expresses a cytokine.

9. The combination according to claim 8, wherein the cytokine is selected form the group consisting of interleukin-2, interleukin-12, interferon-gamma, or a combination thereof.

10. The combination of claim 8, wherein the *Mycobacterium* cell co-expresses two or more cytokines.

11. The combination of claim 10, wherein the *Mycobacterium* cell co-expresses interleukin-2 and interferon-gamma.

12. The combination of claim 1, wherein the virus antigen is a protein antigen of HCV, HIV-1, HBV or influenza.

13. The combination of claim 1, wherein the parasite antigen is gp190/MSP1 protein of *Plasmodium falciparum*.

14. The combination of claim 1, wherein the bacterial antigen is antigen 85 of *M. tuberculosis, M. bovis, M. canetti, M. africanum* or *M. paratuberculosis*.

15. A pharmaceutical composition comprising the combination of claim 1 and optionally a pharmaceutically acceptable carrier.

16. A Th1 immune response-eliciting combination comprising a first constituent, wherein the first constituent is a bacterial cell active as an adjuvant which comprises at least one recombinant nucleic acid molecule encoding a *Listeria* phagolysosomal escape peptide or a *Listeria* phagolysosomal escape polypeptide, wherein the bacterial cell is a urease-deficient *Mycobacterium* cell and
    a separate second constituent, wherein the second constituent is a eukaryotic cell or a genetically manipulated eukaryotic cell which expresses one or more cytokines, wherein the combination elicits the Th1 immune response in a mammal.

17. The combination of claim 16, wherein the one or more cytokines are selected from the group consisting of interleukin-2, interleukin-12, interferon-gamma, or a combination thereof.

18. A method of eliciting a Th1 immune response in a mammal comprising administering to the mammal a Th1 immune response-inducing amount of the combination of claim 1, thereby eliciting the Th1 immune response in the mammal.

* * * * *